(12) United States Patent
Hartdegen et al.

(10) Patent No.: US 9,924,984 B2
(45) Date of Patent: Mar. 27, 2018

(54) POLYAXIAL LOCKING HOLE

(71) Applicant: CROSSROADS EXTREMITY SYSTEMS, LLC, Memphis, TN (US)

(72) Inventors: Vernon Hartdegen, Collierville, TN (US); Michael Hollis, Collierville, TN (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 0 days.

(21) Appl. No.: 15/105,449

(22) PCT Filed: Dec. 16, 2014

(86) PCT No.: PCT/US2014/070495
§ 371 (c)(1),
(2) Date: Jun. 16, 2016

(87) PCT Pub. No.: WO2015/095126
PCT Pub. Date: Jun. 25, 2015

(65) Prior Publication Data
US 2016/0317199 A1    Nov. 3, 2016

Related U.S. Application Data

(60) Provisional application No. 61/919,069, filed on Dec. 20, 2013.

(51) Int. Cl.
*A61B 17/80* (2006.01)
*A61B 17/72* (2006.01)
(Continued)

(52) U.S. Cl.
CPC ...... *A61B 17/7233* (2013.01); *A61B 17/0401* (2013.01); *A61B 17/7037* (2013.01); *A61B 17/8052* (2013.01); *A61B 2017/0427* (2013.01)

(58) Field of Classification Search
CPC ............ A61B 17/80; A61B 17/8033–17/8057
(Continued)

(56) References Cited

U.S. PATENT DOCUMENTS 2,010,913 A * 8/1935 Bruce ................... B23G 5/04
408/221
5,578,034 A * 11/1996 Estes .................. A61B 17/8047
411/909

(Continued)

FOREIGN PATENT DOCUMENTS

FR          2874316       2/2006

*Primary Examiner* — Eduardo C Robert
*Assistant Examiner* — Michelle C Eckman
(74) *Attorney, Agent, or Firm* — David Meibos; Maywood IP Law

(57) ABSTRACT

An implant comprising a multi-directional locking mechanism that allows a bone fixation device, such as a screw, to be rigidly affixed to the implant in a plurality of angles relative to the implant. The implant can be a bone plate, a component of a joint prosthesis or the like. The locking mechanism comprises a passage hole in the implant for passage of a bone fixation device therethrough. One or more beam members are arranged adjacent the passage hole and a space is associated with each beam member. Each space allows the associated beam member to move into or about the space upon axial and/or radial deformation of the beam member caused by fastening the bone fixation device to a bone. The beam members and associated elements of the locking mechanism are sufficiently thin to permit axial and/or radial deformation. And said deformation causes the fixation device to be locked in place relative to the implant.

19 Claims, 28 Drawing Sheets

(51) Int. Cl.
*A61B 17/04* (2006.01)
*A61B 17/70* (2006.01)

(58) Field of Classification Search
USPC .................. 606/280, 286–287, 290–291
See application file for complete search history.

(56) References Cited

U.S. PATENT DOCUMENTS

| | | | |
|---|---|---|---|
| 5,785,713 A | 7/1998 | Jobe | |
| 6,322,562 B1 | 11/2001 | Wolter | |
| 6,974,461 B1 | 12/2005 | Wolter | |
| 7,311,712 B2* | 12/2007 | Dalton | A61B 17/7059 606/287 |
| 7,766,948 B1* | 8/2010 | Leung | A61B 17/8014 606/291 |
| 7,963,982 B2* | 6/2011 | Kirschman | A61B 17/8052 606/291 |
| 8,114,139 B2* | 2/2012 | Sournac | A61B 17/7059 606/286 |
| 8,486,116 B2* | 7/2013 | Heilman | A61B 17/8047 606/286 |
| 8,585,743 B2* | 11/2013 | Ampuero | A61B 17/8605 606/290 |
| 8,728,128 B2* | 5/2014 | Hawkes | A61B 17/7059 606/290 |
| 8,728,129 B2* | 5/2014 | Fritzinger | A61B 17/8047 606/104 |
| 9,603,641 B2* | 3/2017 | Hulliger | A61B 17/8052 |
| 2001/0028148 A1 | 10/2001 | White | |
| 2003/0083663 A1* | 5/2003 | Goldhahn | A61B 17/68 606/291 |
| 2003/0225409 A1* | 12/2003 | Freid | A61B 17/7059 606/281 |
| 2004/0127896 A1* | 7/2004 | Lombardo | A61B 17/8042 606/290 |
| 2004/0127901 A1* | 7/2004 | Huebner | A61B 17/8042 606/281 |
| 2004/0220570 A1* | 11/2004 | Frigg | A61B 17/80 623/17.15 |
| 2005/0165400 A1 | 7/2005 | Fernandez | |
| 2006/0122604 A1* | 6/2006 | Gorhan | A61B 17/8038 606/86 B |
| 2006/0200147 A1* | 9/2006 | Ensign | A61B 17/8047 606/281 |
| 2006/0235400 A1* | 10/2006 | Schneider | A61B 17/8052 606/287 |
| 2006/0241612 A1 | 10/2006 | Medoff | |
| 2006/0241618 A1* | 10/2006 | Gasser | A61B 17/8047 606/287 |
| 2008/0200955 A1 | 8/2008 | Tepic | |
| 2008/0275510 A1 | 11/2008 | Schonhardt et al. | |
| 2008/0300637 A1* | 12/2008 | Austin | A61B 17/74 606/290 |
| 2009/0024170 A1* | 1/2009 | Kirschman | A61B 17/8052 606/280 |
| 2009/0054930 A1* | 2/2009 | Aflatoon | A61B 17/7059 606/246 |
| 2009/0143824 A1* | 6/2009 | Austin | A61B 17/8057 606/280 |
| 2009/0182383 A1* | 7/2009 | Prybyla | A61B 17/8047 606/280 |
| 2009/0281543 A1 | 11/2009 | Orbay et al. | |
| 2009/0312803 A1* | 12/2009 | Austin | A61B 17/8014 606/305 |
| 2010/0125301 A1 | 5/2010 | Kinmon et al. | |
| 2010/0133316 A1 | 6/2010 | Lizee et al. | |
| 2011/0054542 A1 | 3/2011 | Kevin et al. | |
| 2011/0098754 A1 | 4/2011 | Hulliger et al. | |
| 2011/0118742 A1* | 5/2011 | Hulliger | A61B 17/8047 606/70 |
| 2011/0172666 A1 | 7/2011 | Heilman | |
| 2011/0184415 A1* | 7/2011 | Anderson | A61B 17/7059 606/70 |
| 2011/0202092 A1 | 8/2011 | Frigg et al. | |
| 2011/0270326 A1* | 11/2011 | Black | A61B 17/8038 606/308 |
| 2011/0295324 A1 | 12/2011 | Donley et al. | |
| 2011/0319942 A1 | 12/2011 | Bootland et al. | |
| 2012/0053638 A1* | 3/2012 | Rusch | A61B 17/8047 606/287 |
| 2012/0059425 A1* | 3/2012 | Biedermann | A61B 17/8042 606/291 |
| 2012/0065690 A1* | 3/2012 | Perrow | A61B 17/7059 606/294 |
| 2012/0136396 A1 | 5/2012 | Baker et al. | |
| 2012/0143193 A1 | 6/2012 | Hulliger | |
| 2012/0191141 A1 | 7/2012 | Costabile | |
| 2012/0323284 A1 | 12/2012 | Baker et al. | |
| 2013/0026207 A1 | 1/2013 | Fox | |
| 2013/0150900 A1* | 6/2013 | Haddad | A61B 17/809 606/290 |
| 2014/0018862 A1* | 1/2014 | Koay | A61B 17/8057 606/281 |
| 2014/0222086 A1 | 8/2014 | Kuster | |
| 2015/0216573 A1* | 8/2015 | Chin | A61B 17/7059 606/279 |
| 2015/0320462 A1* | 11/2015 | Biedermann | A61B 17/8057 606/291 |
| 2016/0089191 A1* | 3/2016 | Pak | A61B 17/8052 606/291 |
| 2017/0065312 A1* | 3/2017 | Lauf | A61B 17/8047 |

* cited by examiner

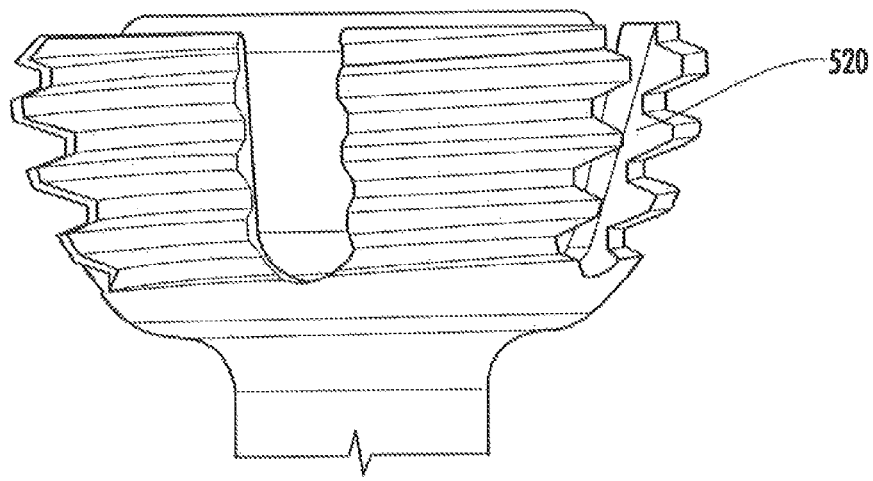
FIG. 26
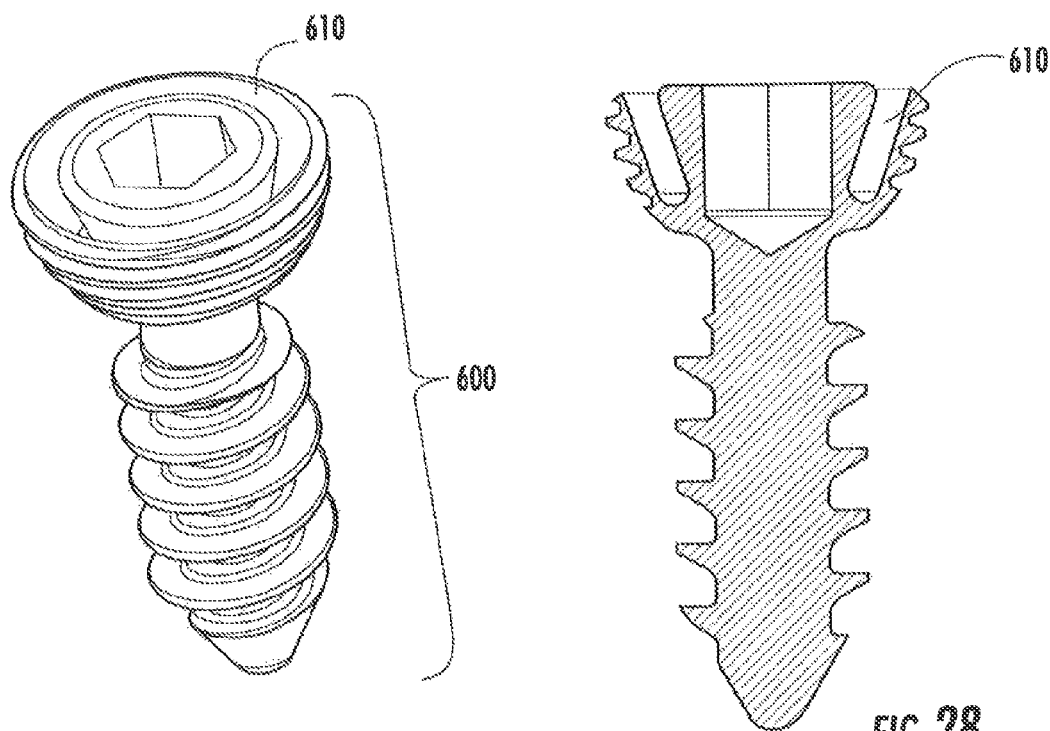
FIG. 27
FIG. 28

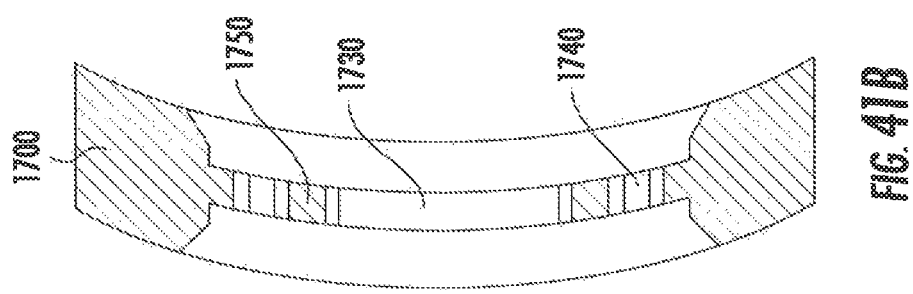
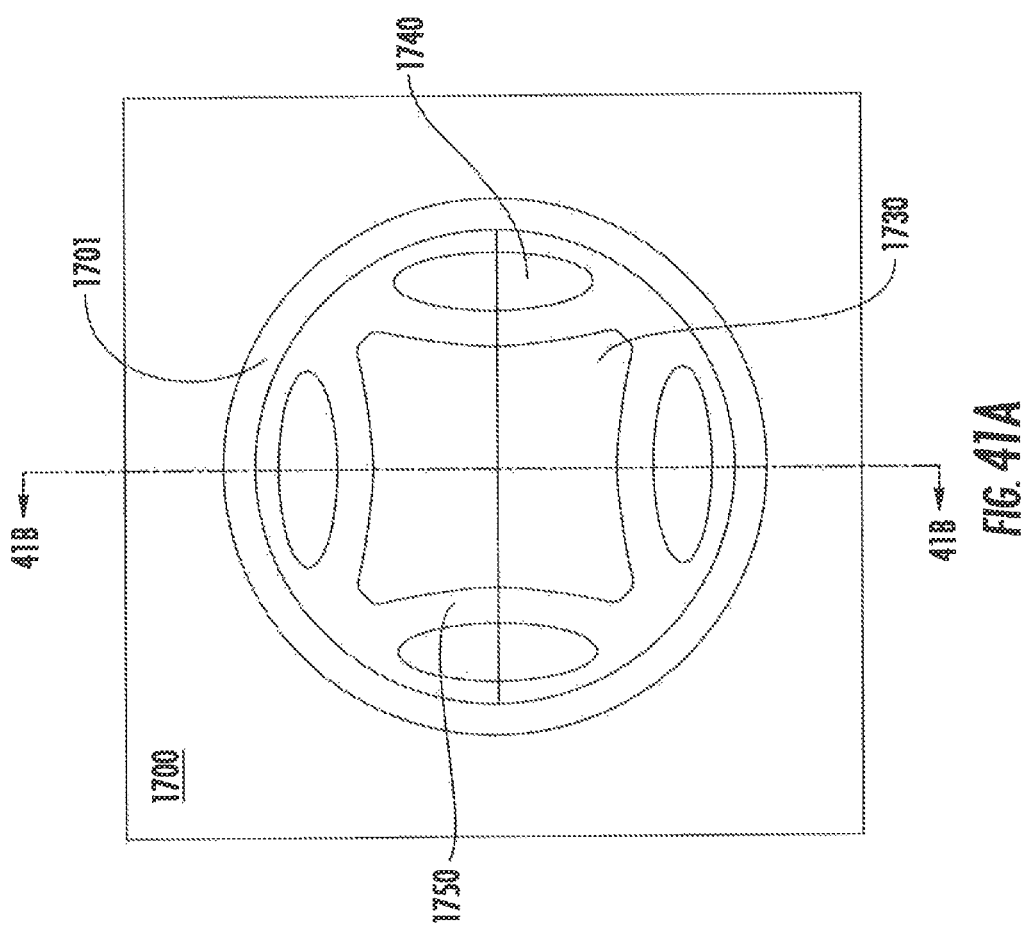

POLYAXIAL LOCKING HOLE

CROSS REFERENCE TO RELATED APPLICATION

This is a non-provisional application claiming priority of provisional application Ser. No. 61/919,060 filed Dec. 20, 2013.

BACKGROUND OF THE INVENTION

Field of the Invention

The present invention is in the technical field of implanted medical devices. More particularly, the present invention relates to a multi-directional locking mechanism that can be incorporated in any kind of implant device that needs to be fastened to a bone, including fractured bones and bones that are not fractured. For example, the multi-directional locking mechanism can be incorporated into fixation systems for bones of all types which use plates and screws and other implants such as prostheses that are affixed to bones with screws. Such fixation systems are used in osteosynthesis (bone fusion), wherein bone screws are connected to a bone and a plate which bridges the fracture. It is desirable for optimal alignment onto the bone fragments, or for compensating target errors, to be able to incorporate the bone screws at different angles into the plate.

The Related Art

Implants of various types may be indicated for the entire skeleton. Implants include bone plates, intramedullary nails, suture anchors and prostheses of various types including joint prostheses and elements thereof such as acetabular cups for hip replacement prostheses. A "bone fixation device" may include any of a variety of devices that secure an object to a bone, including but not limited to bone screws, pins, blades and the like.

The present invention seeks to remedy the problems of the prior art. The invention provides a multi-directional locking mechanism in the fastener hole (also referred to herein as a "hole" or "passage hole" or "through hole") of an implant, without the need for additional components, that can accommodate conventional locking screws in a plurality of angles in a stable manner. The invention allows, for example, the overall thickness of a bone plate to be minimal providing for a low profile locking plate. Unlike the prior art, the invention is not required to rely on cross threading, gouging or stripping of the fastener hole threads and the bone screw threads. Also, the invention may create negative space around the periphery of the fastener hole to accommodate displaced material when the screw head engages features of the fastener hole to create a locked condition. This space may be created by a beam member (sometimes referred to herein as a "beam") that is connected to the body of the implant. The space and beam configuration can be any geometry or combination of geometries as will be apparent to those having skill in the art based upon the disclosures herein. At least one space and one beam member should advantageously be present. The negative space may allow the beam member to translate both parallel and perpendicular to the axis of the passage hole. Because the beam member is thin, the movement of the beam member along its length may vary. All of these degrees of freedom may be beneficial to accommodate a wide variety of implants.

SUMMARY OF THE INVENTION

The present invention comprises a multi-directional locking mechanism that allows a bone fixation device to be rigidly fixed to an implant in a plurality of relative angles.

More specifically, the invention comprises, for use on an implant, one or more multi-directional locking mechanisms, each of which includes a passage hole, a perimeter, at least one beam member, and at least one space. The passage hole and corresponding perimeter can be any geometry, circular or otherwise. The beam member and space can have a plurality of geometries, orientations and configurations. The space(s) around the periphery of the hole accommodate displaced material of the beam member when the bone fixation device engages the beam member. In other words, the bone screw will contact the beam member causing movement of the beam member into or about the negative space. At least one space and one beam member is present in each multi-directional locking mechanism. The periphery of the passage hole has at least one beam member that is allowed to deform or adjust to the bone fixation device thereby locking the bone fixation device to the implant. The term "locking" as used herein can mean complete locking, i.e., axial and rotational locking, or just axial locking which allows rotational movement but no axial movement. When the beam member engages the bone fixation device, the beam or a portion of the beam may move into the negative space. This causes a radial compression force on the bone fixation device which may increase as the device is advanced further into the locking feature. The corresponding bone fixation device is appropriately sized to relatively interfere with the beam feature in a plurality of insertion angles.

One advantage achieved by the invention is that, as a result of the beam members, a bone fixation device can be introduced at an angle that is different from or the same as the specified axis of the hole and rigidly fixed to the implant while maintaining rigidity. Furthermore the invention need not rely on cross threading, gouging, stripping, tapping, differential hardness, or third components, thereby reducing the potential for metal fragments and debris. The multi-directional locking mechanisms of the present invention benefit from material deformation in a predictable manner that allows radial and/or helical movement of the beam member. This is accomplished using a predefined space that accommodates the deformed or moved material. A plurality of bone fixation devices may be used for optimal fixation. The locking mechanisms and/or implants of the present invention can be made from a variety of conventional materials or from materials that previously were not conducive to current state of the art threading options, e.g. nitinol.

By virtue of the beam and predefined space, and a relatively sized bone fixation device, a locking interface is produced between the implant and bone fixation device, even when the bone fixation device is inserted at an angle displaced from the axis of the hole.

The geometry of the surface of the multi-directional locking mechanism may advantageously be constructed to facilitate compatibility with the bone fixation device to be introduced. The beam and/or other deformable features is adjacent to a predefined space, which is created to accommodate the movement of the beam. The space and thinness of the beam member allows the beam member to move in six degrees of freedom including radial and helical movement. The radial movement is uniquely advantageous over known locking mechanisms, which do not provide radial movement. The helical or complex deformation is also uniquely advantageous because it allows the deformed beam member to "match up" with the bone screw. The degrees of freedom and the predefined space thereby can adjust and/or move to accommodate the bone fixation device in a manner that provides relatively rigid fixation. The beam member is allowed to move or deflect in a manner that generally maintains the parallel nature of the opposing faces of the beam member. The multi-directional locking mechanism may be independent of the seating surface. Due to the plurality of possible combinations and movements, the bone fixation device "creates" its own proper seating position and geometry within the implant and locking mechanism. Said another way—the beams of the locking feature conform to the chosen trajectory of the bone fixation device.

The beam and predefined space may have a shape to facilitate screw insertion. For example, a portion of the face or the entire face of the beam may be concave, spherical, tapered or contain a lead-in angle. This shape facilitates the insertion of a bone fixation device in such a manner that, in response to contact of the bone fixation device with the beam, the bone fixation device is automatically pulled into the hole in the implant without exerting a significant compression force to engage the two devices. This shape also allows the beam member to move in such a way that it creates a path for the mating feature on the bone fixation device.

Any number of multi-directional locking mechanisms may be arranged radially symmetrically, non-radially symmetrically or radially but non-symmetric around the periphery of the passage hole. The passage hole may or may not be circular. The predefined space may be closed about its perimeter, or could have a small opening to the passage hole.

In this specification the term "radial deformation" means the deformation of a beam member as it moves perpendicular to and away from the axis of the fastener hole. The terms "axial deformation" or "helical deformation" mean the deformation of a beam member as it moves in parallel with the axis of the fastener hole. Deformation may be more complex where a particular beam member may not deform uniformly. Both axial and helical deformation can and often do occur simultaneously according to the present invention.

BRIEF DESCRIPTION OF THE DRAWINGS

FIG. 26 is a partial front view of the embodiment shown in FIG. 24.

FIG. 27 is a perspective view of a bone fixation device with a predefined space and a beam member according to a fifth embodiment of the invention.

FIG. 28 is a cross section view of the embodiment shown in FIG. 27.

FIGS. 41A and 41B illustrate an embodiment of a locking mechanism in a curved bone plate.

DETAILED DESCRIPTION OF THE PREFERRED EMBODIMENTS

The embodiments described herein may be used in connection with any type of implant, including but not limited to bone plates such as various trauma plates and reconstruction plates, in numerous applications such as foot and ankle, upper extremity, rib fractures, pelvic fractures, maxillofacial, etc. The bone plates may be curved, contoured, straight, or flat and may be of a particular shape for a particular anatomy or a more general shape for multiple anatomies. The bone plates may be provided precontoured or manipulated and/or contoured during use for a specific application.

Figure 1:
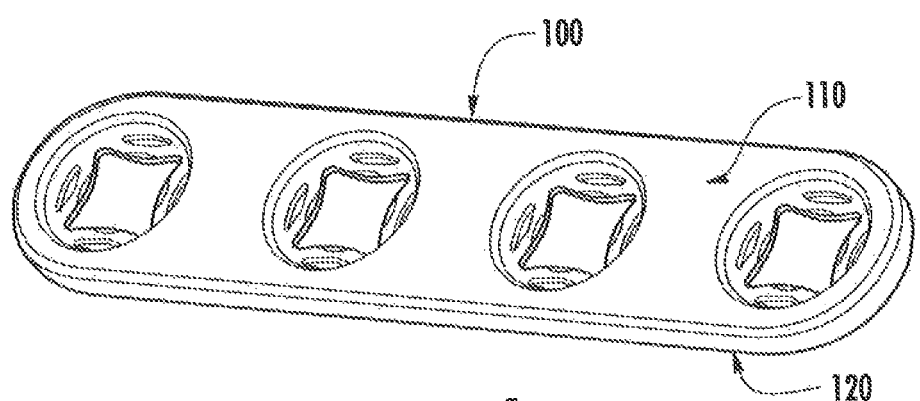
FIG. 1 is a perspective view of a bone plate with multiple openings having beam members according to a first embodiment of the invention.

The bone plate 100 shown in FIG. 1 is a simple generic plate. The bone plate may have a head portion that is contoured to match a particular bone surface, such as a metaphysis or diaphysis, it may have projections from the shaft, be available in typical shapes (L-shape, T-shape, Y-shape, etc.) or may form any other appropriate shape to fit the bone/fracture to be treated. The cross-section of the bone plate 100 may be flat as shown in FIG. 1 or contoured (such as a one-third tubular shape or similar). The bone plate 100 may be may be comprised of titanium, stainless steel, nitinol, cobalt chrome, carbon composite, plastic or polymer (e.g. PEEK, UHMWPe), resorbable materials (such as PLA, PGA) or some combination of these materials or any other appropriate material that has sufficient strength for the intended application, while also having sufficient biocompatibility for implantation in the body. It should be understood that bone plates comprised of any appropriate material are within the scope of this invention.

Figure 2:
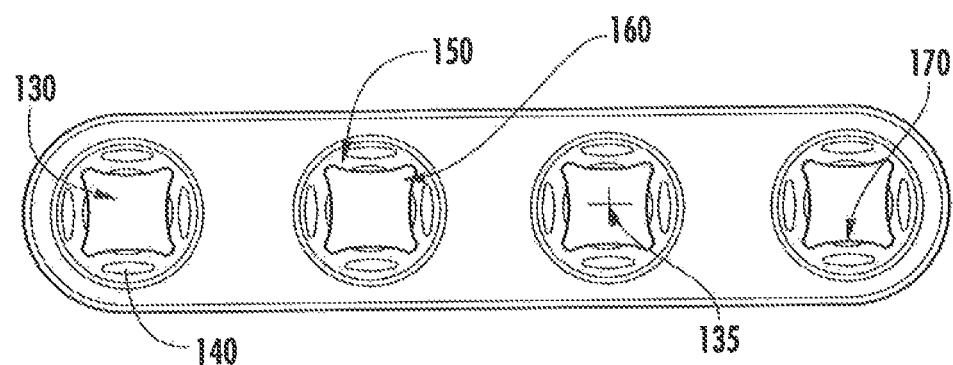
FIG. 2 is a top plan view of the bone plate of FIG. 1.
Figure 3:
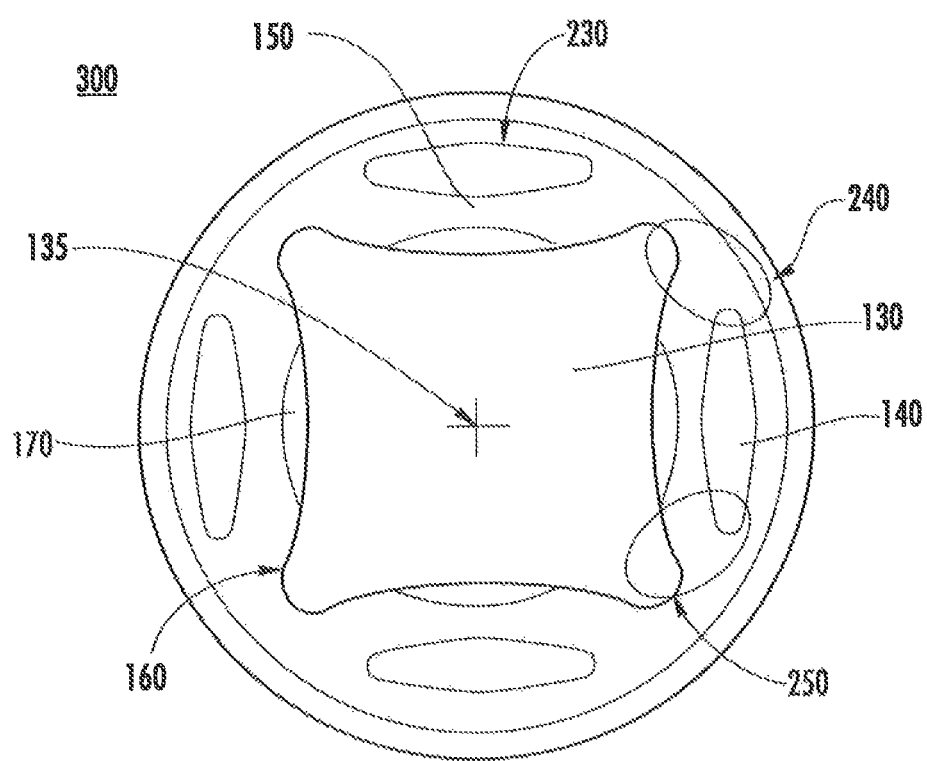
FIG. 3 is a detailed view illustrating the beam members according to the first embodiment of the invention.
Figure 4:
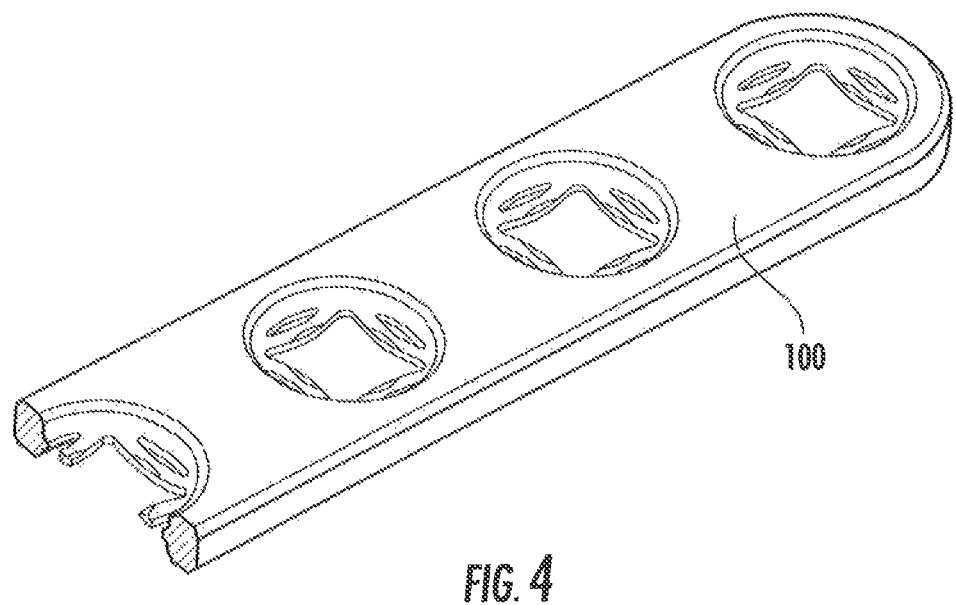
FIG. 4 is a perspective view, with an included cross-section view of a bone plate with multiple openings having beam members according to the first embodiment of the invention.

A first embodiment of the invention is illustrated in FIGS. 1 and 2 and the locking mechanism 300 thereof is illustrated by itself in FIG. 3. Bone plate 100 has at least one opening 130 that accepts the bone fixation device 390 (see FIG. 11). Opening 130 has a central axis 135. The multi-directional locking mechanism 300 illustrated in FIG. 3 comprises the passage hole 130, its central axis 135, at least one beam member 150, and at least one predefined space 140. The opening 130 provides polyaxial fixation, and thus is adapted to receive a bone fixation device in a plurality of angles. The opening can also accommodate the bone fixation device straight in as well. Predefined space 140 may or may not pass through all or some of upper and lower surfaces, for example, upper and lower surfaces 110, 120, 180, 190, 1010 and 1020. (See FIGS. 1, 6 and 8.) Stated another way, the predefined space 140 may be a pocket, enclosed space, blind hole, through hole, or a combination of the foregoing. For example, FIGS. 37A-37D illustrate and embodiment where the predefined space is a blind hole. The periphery 160 of passage hole 130 may have various shapes. The shape of the passage hole may be adapted to receive the head 400 of the bone fixation device 390. The periphery of the passage hole 130 contains at least one beam member 150 and one predefined space 140. The periphery 230 of the predefined space 140 may have any appropriately sized geometry. In other words, the geometry must be sized and configured to allow enough space for the beam member to move into when it is deformed by a fixation device. The beam member may move partially or completely into the predefined space 140. Movement of the beam member 150 into the predefined space may be such that the beam member bottoms out, abuts, or significantly closes the predefined space 140. The beam member may move partially or completely into the negative space. It may be desirable for the beam member to bottom out, abut, or significantly close the negative space. Bottoming out may provide a "stop" to the movement of the beam member thereby giving more rigidity to the assembled construct. Beam member 150 has a first beam connection 240 and a second beam connection 250 encircled by the ovals designated by the reference numerals 240 and 250. The beam connections join the beam 150 to the remainder of the locking mechanism. Beam member 150 may have an optional lead-in feature 170 in the form of a thinned portion on the edge adjacent the passage hole. The lead-in feature can be on the top surface or the bottom surface or the top surface and bottom surface of the beam member, to facilitate engagement with the head 400 of the bone fixation device 390. The figures show a passage hole and locking mechanism that are orthogonal to the plate top surface 110. However, alternate embodiments could have the passage hole and/or locking mechanism not orthogonal to the bone plate as illustrated in FIGS. 39A-39C and 40A-40C.

The locking mechanism 300 shown in FIG. 3 shows four beam members 150 and four predefined spaces 140. Any combination and orientation of any number of beam members and predefined spaces are within the scope of this invention.

Figure 5:
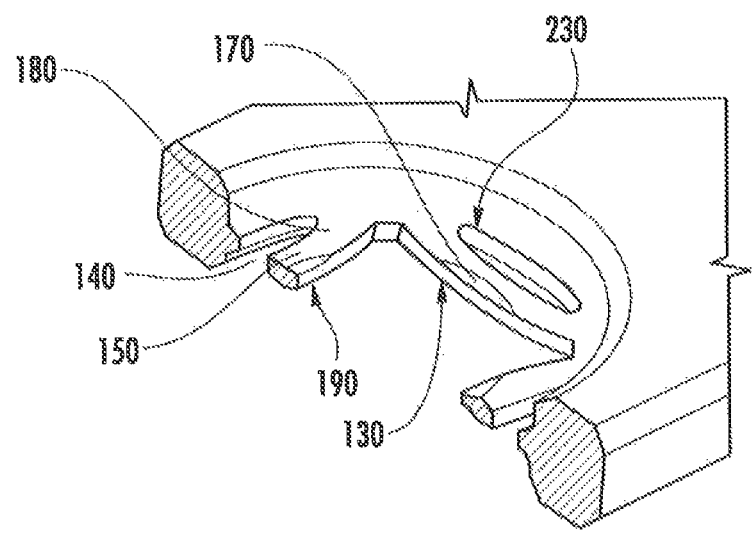
FIG. 5 is a detailed view of the cross-section in FIG. 4.
Figure 6:
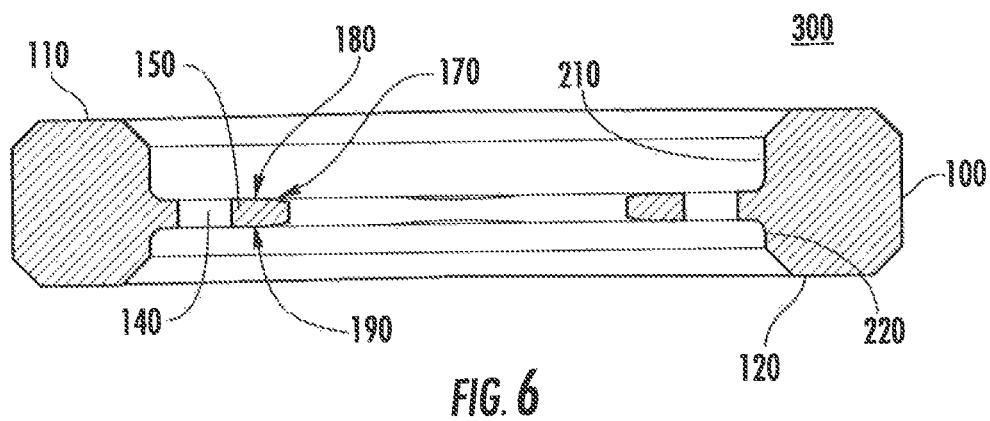
FIG. 6 is a front plan view of the cross section in FIGS. 4 & 5.
Figure 7:
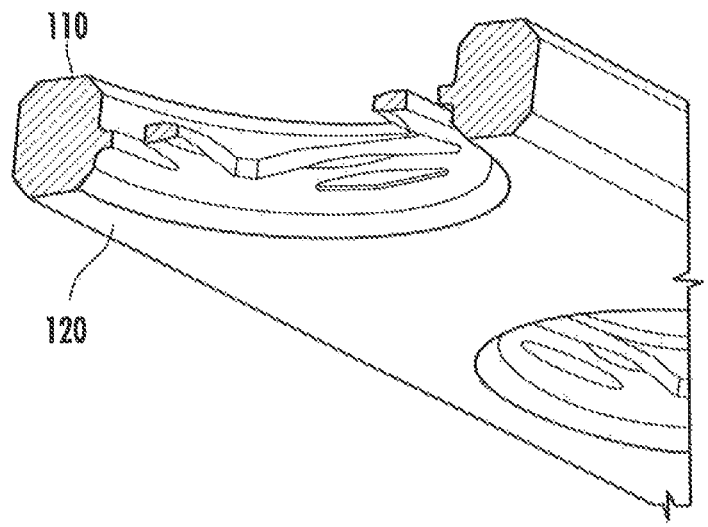
FIG. 7 is a bottom perspective view of a portion of FIG. 4.

FIGS. 5, 6 and 7 illustrate various views of a cross-section of the first embodiment of the invention. The locking mechanism 300 is positioned between an upper recess 210 and a lower recess 220. The locking mechanism 300 may be equally spaced between the upper surface 110 and the lower surface 120, or may be closer to the upper surface 110 or the lower surface 120, as shown in FIG. 6. The locking mechanism 300 may also be biased completely towards the upper surface 110 or lower surface 120. The upper recess 210 and the lower recess 220 are shown as cylindrical counterbores, but could also be countersinks, tapered, spherical, parabolic, or any other appropriate shape. Upper recess 210 and lower recess 220 are shown to have similar geometry but could have different geometries or combinations of geometries.

FIG. 5 shows the beam members 150 and predefined spaces 140 in the same plane. The current invention may also include beam members and predefined spaces that are in different planes within the same locking mechanism. Stated differently, within a particular hole one beam member/predefined space combination may be on a different plane than another beam member/predefined space combination or the beam members in one hole may be on a different plane than another hole within the same implant. This may be advantageous to facilitate locking between the locking mechanism 300 and the bone fixation device 390, for example, in cases where the shape of the implant may be more contoured, it may be necessary to have different beam members and predefined spaces on different planes to provide the necessary engagement between the implant and the fixation device. An example is in the acetabular cup illustrated in FIGS. 41A, 41B and 43-46.

Figure 31:
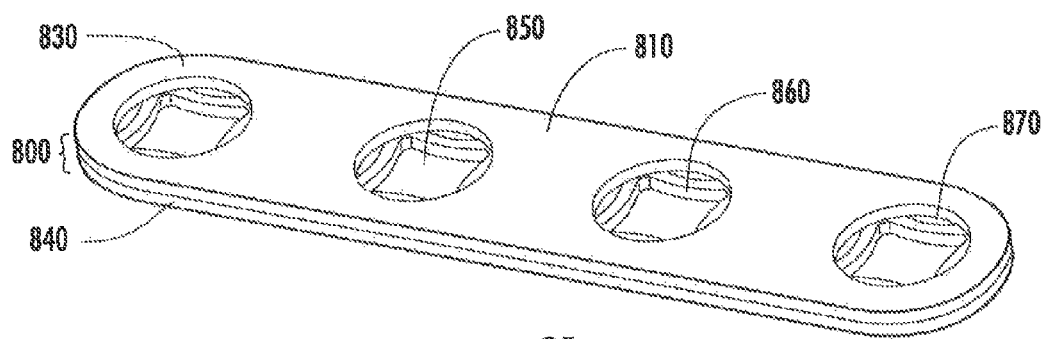
FIG. 31 is a perspective top view of a laminate bone plate incorporating a multi-directional locking mechanism of the current invention.
Figure 32:
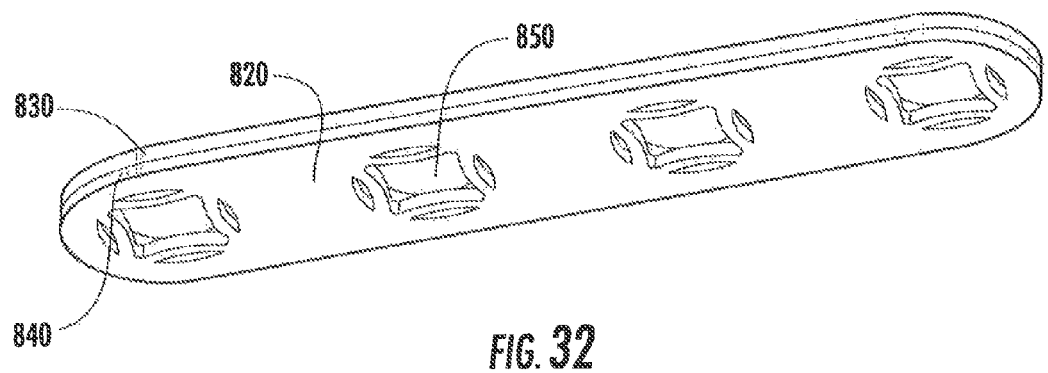
FIG. 32 is a perspective bottom view of the laminate bone plate of FIG. 31.

FIG. 6 shows a bone plate 110 constructed of one piece. However, the plate could be a laminate construction made of two or more layers as shown in FIGS. 31 and 32. Laminate construction may be advantageous in the manufacturing of the plate geometry with the locking mechanism. The features of the locking mechanism could be manufactured on one layer or multiple layers.

Figure 8:
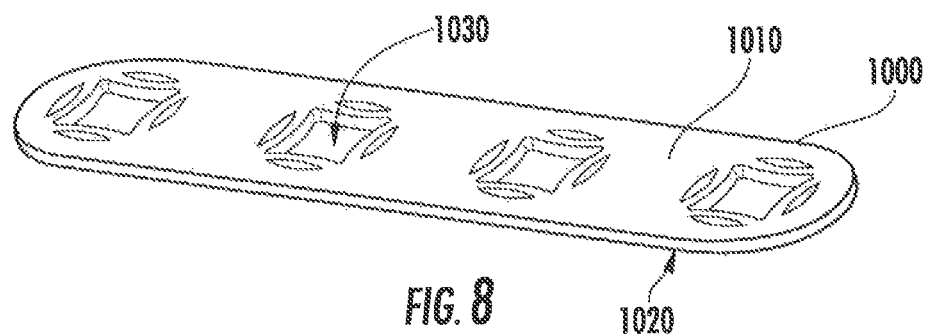
FIG. 8 is a perspective view of a bone plate with multiple openings having beam members according to a second embodiment of the invention.
Figure 9:
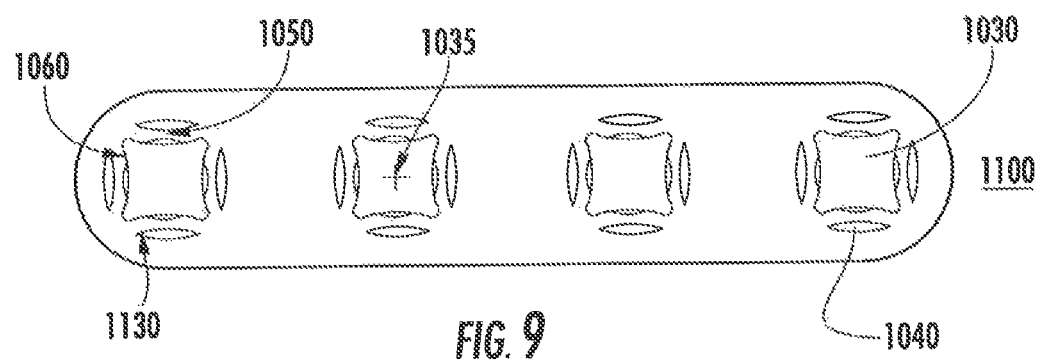
FIG. 9 is a top plan view of the bone plate of FIG. 8.
Figure 10:
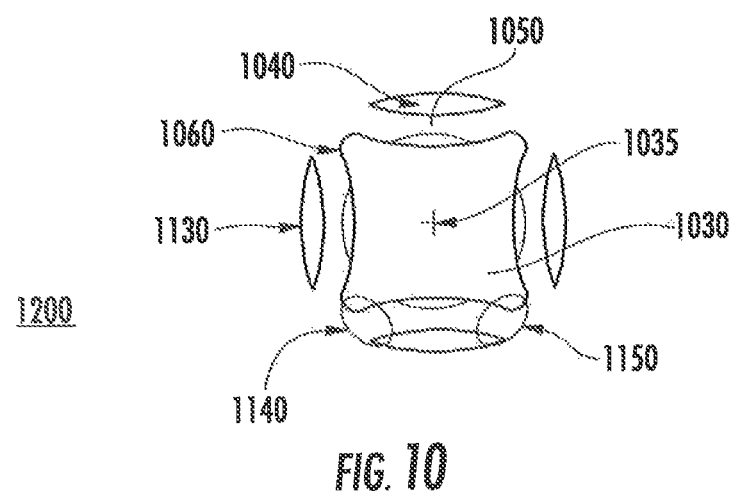
FIG. 10 is a detailed view of the beam members according to FIG. 8.
Figure 38A:
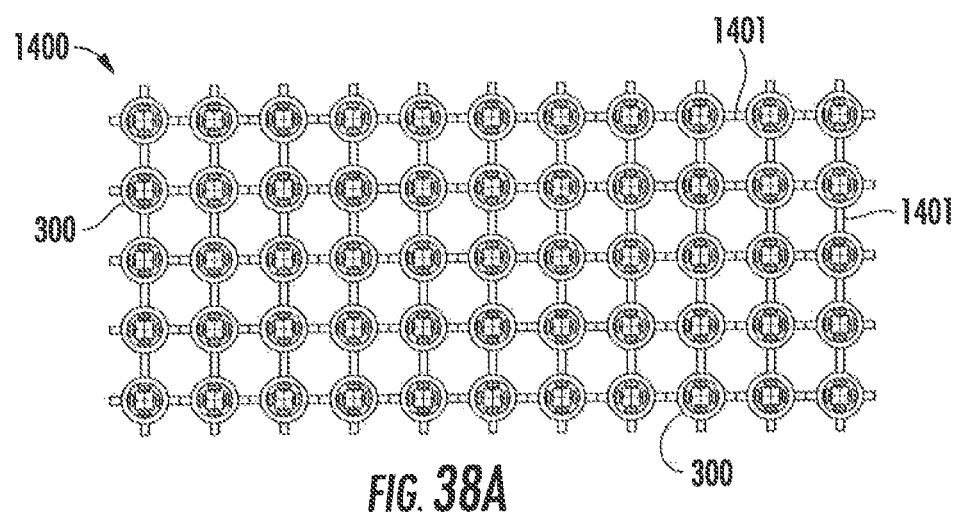
FIGS. 38A and 38B illustrate a mesh embodiment comprising multiple locking mechanisms of the invention.
Figure 38B:
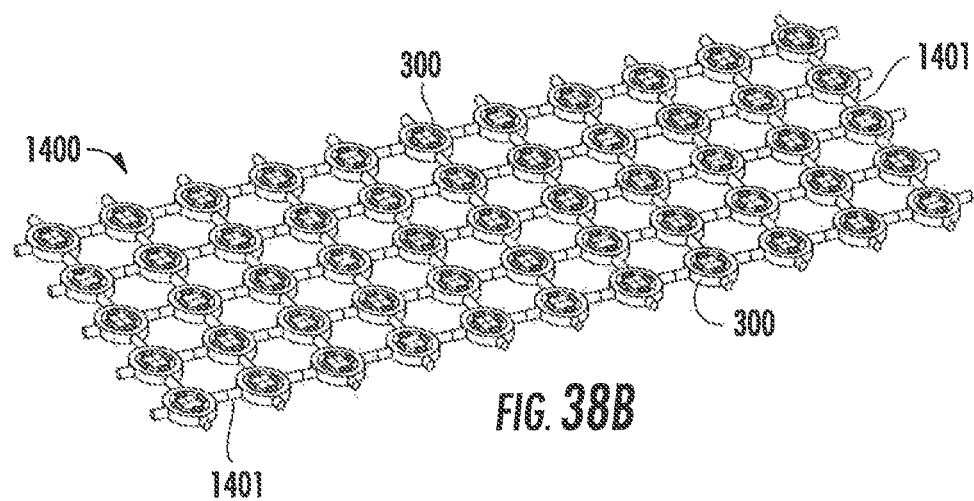

A second embodiment of the invention is shown in FIGS. 8 and 9. Bone plate 1000 has at least one opening 1030 that accepts a bone fixation device 390 (see FIG. 11). Opening 1030 has a central axis 1035. The locking mechanism 1200 illustrated in FIG. 10 includes a passage hole 1030, which has a central axis 1035, at least one beam member 1050, and at least one predefined space 1040. The locking feature 1200 is adapted to receive a bone fixation device in a plurality of angles. The periphery 1060 of passage hole 1030 may have various shapes. The shape of the passage hole may be adapted to the appropriately sized head 400 of the bone fixation device 390. The periphery of the passage hole 1030 contains at least one beam member 1050 and one predefined space 1040. The periphery 1130 of the predefined space 1040 may be any appropriately sized geometry to allow movement of the beam member into the predefined space either partially or completely, thereby allowing the lock to occur. Beam member 1050 has a first beam connection 1140 and a second beam connection 1150 (the reference numerals 1140 and 1150 designate ovals drawn around the areas of connection) that join the beam 1050 to the locking mechanism. Beam member 1050 may or may not have a lead-in feature (such as 170 in FIG. 6) to facilitate engagement with the head 400 of the bone fixation device 390. One advantage of the embodiment shown in FIGS. 8-10 is the thinness of the locking mechanism. The thin device may not have an upper recess or lower recess (210 and 220 as shown in FIG. 1-7). The overall thin profile is advantageous for applications where a low profile implant is needed such as a rib fracture plate or in maxillofacial applications. One advantage of the present invention is that the function of the locking mechanisms 1200 and 300 is independent of the overall thickness of the plate. Other embodiments of bone plate 1000 include a mesh type configuration that would provide a thin mesh type plate with a minimal thickness locking mechanism such as illustrated in FIGS. 38A and 38B. In contrast, known polyaxial locking mechanisms may rely on movement of material in a direction that would affect the overall thickness of the locking mechanism. Due to the predefined space of the current invention, the movement of the material can occur radially and/or axially without affecting the thickness profile of the overall construct. This is particularly advantageous in applications where low profile bone plates are required.

The locking mechanism 1200 shown in FIG. 10 has four beam members 1050 and four predefined spaces 1040. Any combination and orientation of any number of beam members and predefined spaces are within the scope of this invention.

Figure 11:
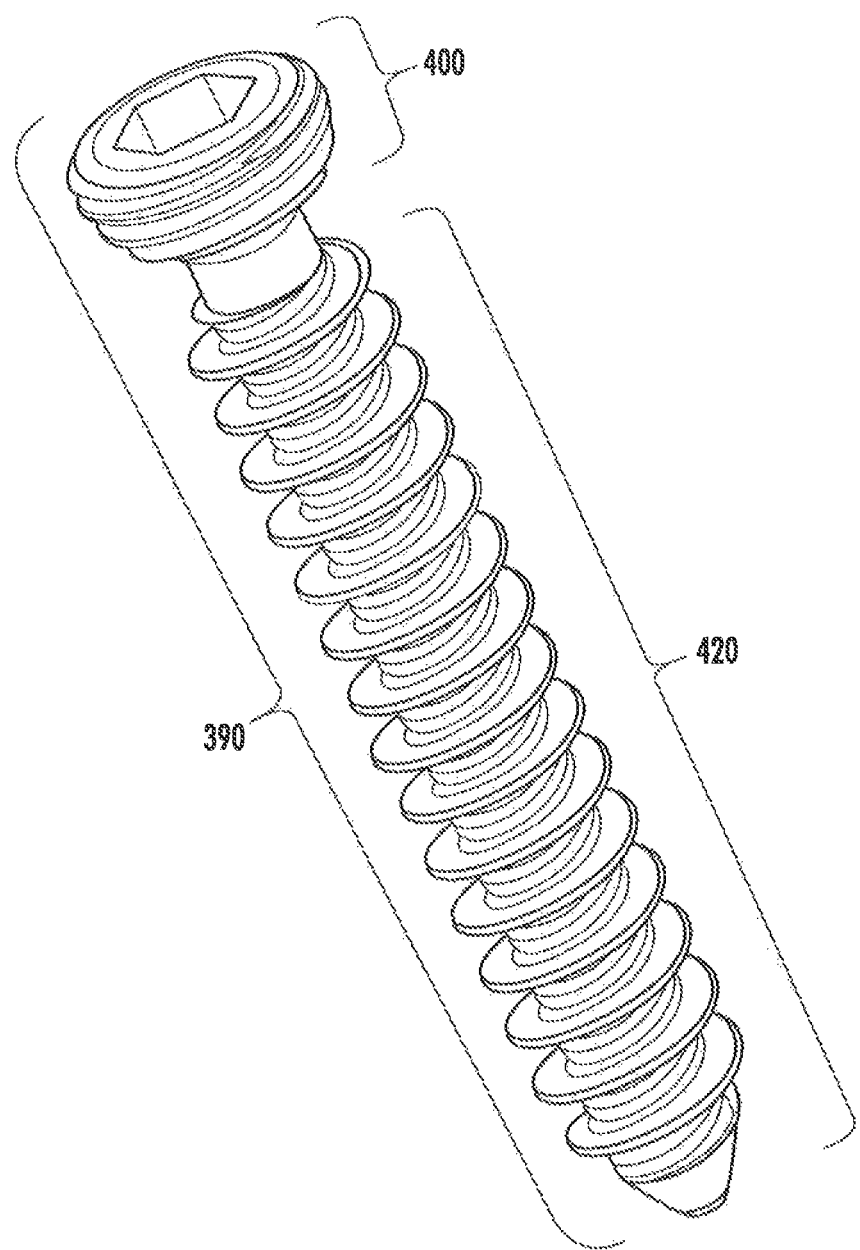
FIG. 11 is a perspective view of a typical orthopedic locking screw.
Figure 12:
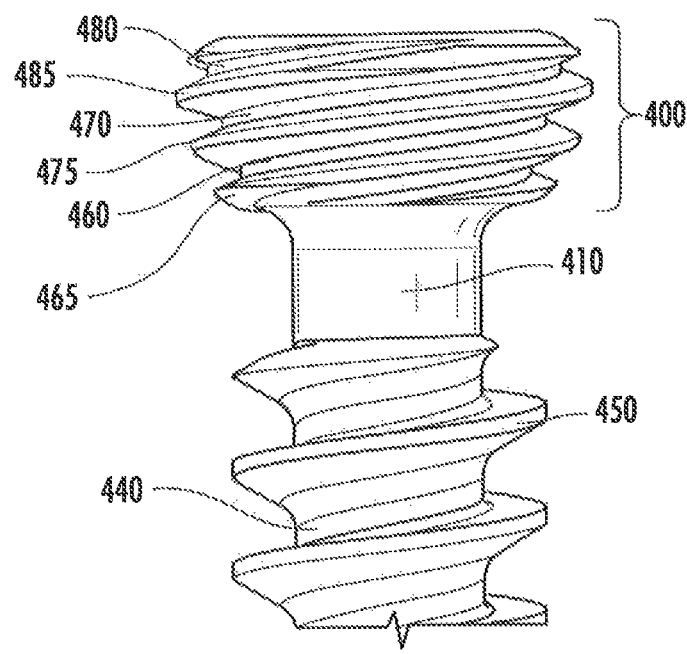
FIG. 12 is a detailed plan view of the screw of FIG. 11.
Figure 13:
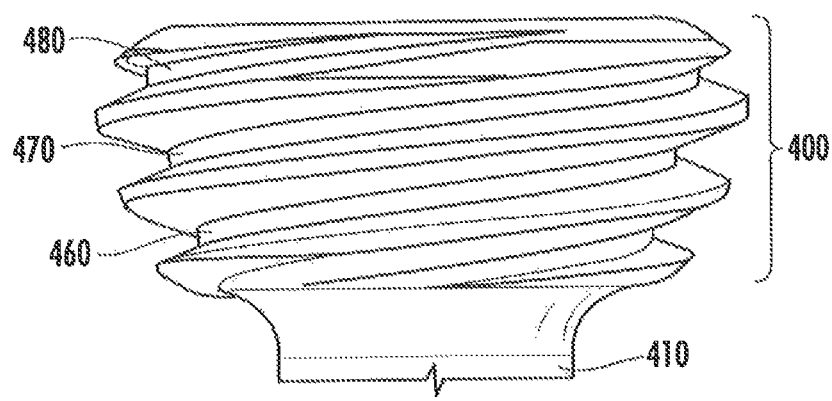
FIG. 13 is close-up plan view of the screw head of FIG. 12.

The locking mechanism shown in FIGS. 3 and 10 include at least one beam member (150 and 1050) that has substantially parallel upper surfaces and lower surfaces. The beam members may be in close proximity to the predefined spaces 140 and 1040, respectively. The size, shape, orientation and configuration of the beam member 150, 1050 and corresponding predefined space 140, 1040 provide an appropriate interference with the head 400 of the bone fixation device 390. The bone fixation device 390 illustrated in FIG. 11 may be any typical, standard locking bone fixation device or a non-locking bone fixation device. However, the embodiments described herein are uniquely advantageous when used with locking bone fixation devices that have a series of threads on their heads. FIGS. 11-13 show an example of a bone fixation device that may be used in accordance with the various embodiments of this invention. As shown in FIG. 11, bone fixation device 390 has a shaft 420 and a head 400. Shaft 420 is threaded but it may be otherwise configured to engage bone. For example, it may be fully threaded or partially threaded, and may include a helical blade and/or one or more tacks, deployable talons, expanding elements, or other bone engagement features known in the art. Any feature that allows shaft 420 to engage bone is considered within the scope of this invention and may be referred to generally as a "threaded shaft" for the sake of convenience. It is also possible, however, that shaft 420 is not threaded, so that bone fixation device 390 takes the form of a peg or a pin. Such alternative embodiments may be preferred in certain procedures, where there is no concern that the bone fixation device may pull out from the bone or where the orientation/position of the peg/pin relative to the plate and other pegs/pins prevents the construct from pulling out of a bone.

Shaft 420 may be cylindrical or non-cylindrical, threaded or non-threaded depending on the application. The minor diameter 440 may have a consistent dimension or may have a varying dimension along its length. For example, for a threaded application, the minor diameter 440 may taper, while the major diameter 450 remains constant. The opposite is also possible.

FIG. 12 shows one embodiment of a bone fixation device that has a tapered head 400. In this particular embodiment, minor diameter 480 is larger than minor diameter 470, which is larger than minor diameter 460. This tapered geometry allows for engagement with the beam member via the first diameter 460. The diameters of 460, 470, and 480 are sized to fit the passage opening 130 or 1030. The larger diameter 480 is sized to prevent the bone fixation device from proceeding through the locking mechanism. As the screw is advanced, the radial compression increases thereby "locking" the bone fixation device to the locking mechanism. In this embodiment the larger diameter 480 is effectively a radial stop. The major diameters of the head 400 are tapered correspondingly with the minor diameters. Major diameter 485 is larger than major diameter 475, which is larger than major diameter 465. The major diameters are appropriately sized to fit within the locking mechanism boundaries of each embodiment. Alternate embodiments may not have a typical threaded geometry. For example, for a unidirectional locking application, the bone fixation device may have a pan head with a cam or groove feature that will engage the locking mechanism. There are numerous alternate embodiments that would be obvious to those skilled in the art with the aid of the present disclosure. One advantage of this locking mechanism is the ability to achieve multi directional, including unidirectional, locking without the need for a threaded feature in the plate. The locking mechanism can also be used with bone fixation devices that are not locking. The shank 410 shown in FIG. 12 may or may not be a distinct feature on an appropriate bone fixation device. The threaded head 400 may transition into the shaft 420 without a smooth shank 410.

Figure 14:
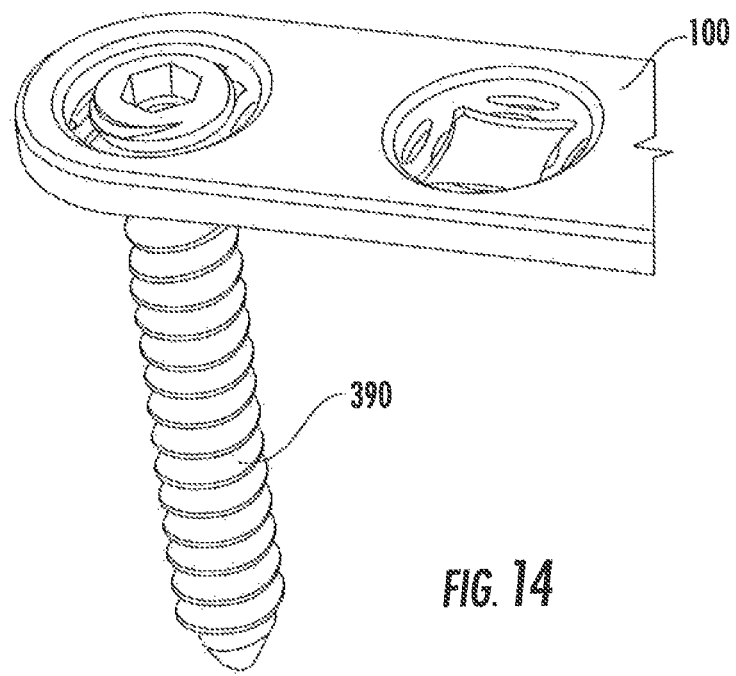
FIG. 14 is a perspective view of the bone screw of FIG. 12 inserted coaxially into a hole of the bone plate with multiple openings having beam members according to the first embodiment of the invention.
Figure 15:
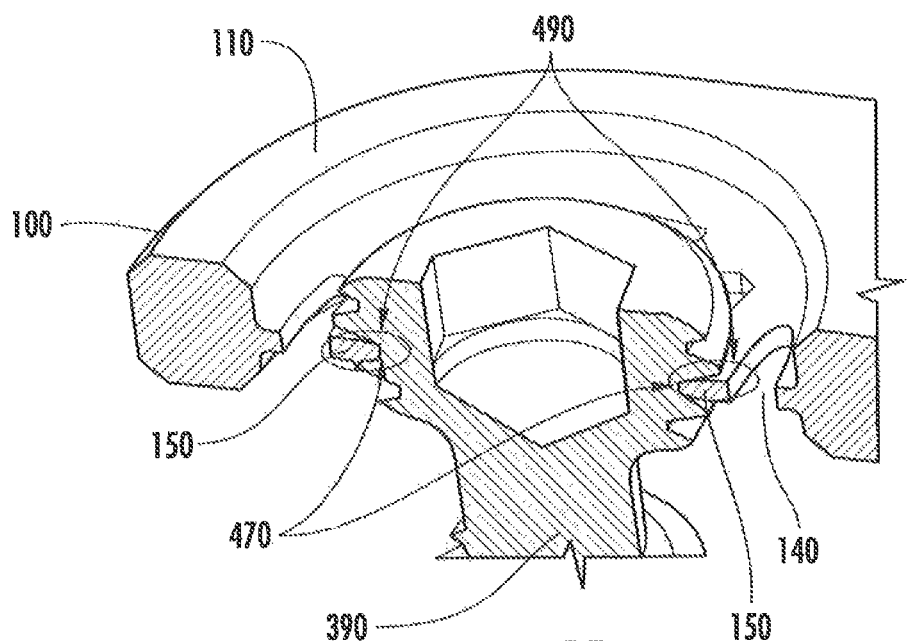
FIG. 15 is a partial cross section view of FIG. 14.
Figure 36A:
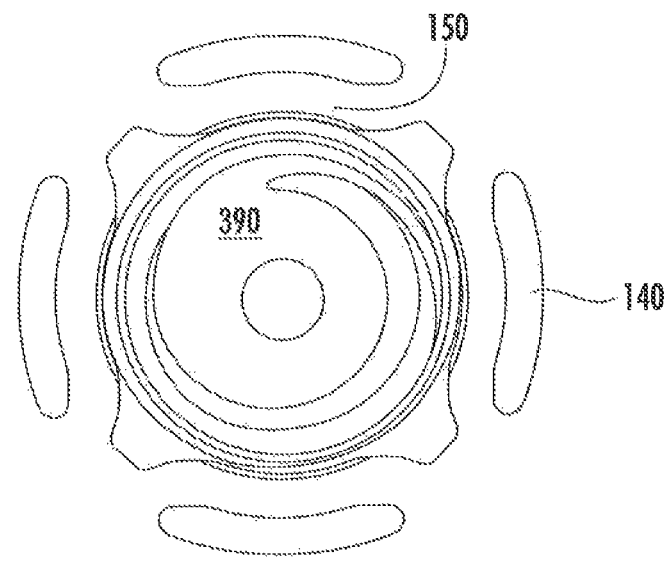
FIGS. 36A and 36B illustrate the deformation of the beam members caused by insertion of a screw perpendicular to a bone plate as in FIGS. 14 and 15.

FIGS. 14 and 15 show an assembly of a bone fixation device 390 and the bone plate 100. The bone fixation device 390 is a bone screw with a threaded head. FIGS. 14 and 15 show the bone fixation device in a neutral or zero degree position. FIG. 15 shows the engagement 490 between the beam member 150 and the head diameter 470. As the head 400 engages the locking mechanism the beam is allowed to move to accommodate the needed engagement. The deformed state of the fixation assembly with fixation device 390 therein is shown in FIG. 36A. In this case, a helical threaded feature is used, but in other embodiments, this could be replaced with a variety of other features including concentric rings, cams, etc. In the present invention, the beam may move into the space above and/or below the beam member; however, the present invention also allows the beam, when engaged with the bone fixation device, to move into the predefined space. Thus, the present invention allows for a radial movement in addition to other degrees of freedom.

Figure 16:
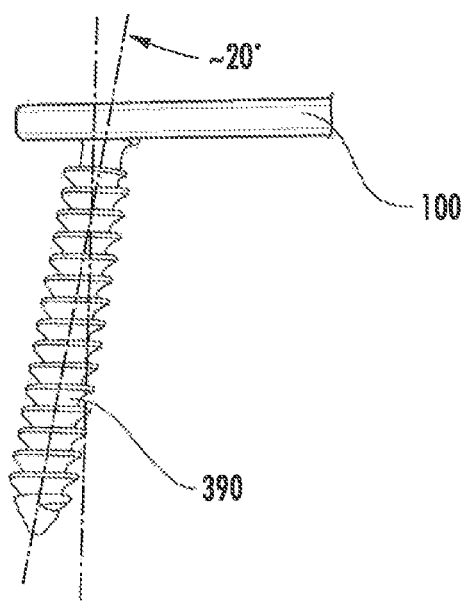
FIG. 16 is a plan view of the bone screw of FIG. 14 inserted non-coaxially into a hole of the bone plate with multiple openings having beam members according to the first embodiment of the invention.
Figure 17:
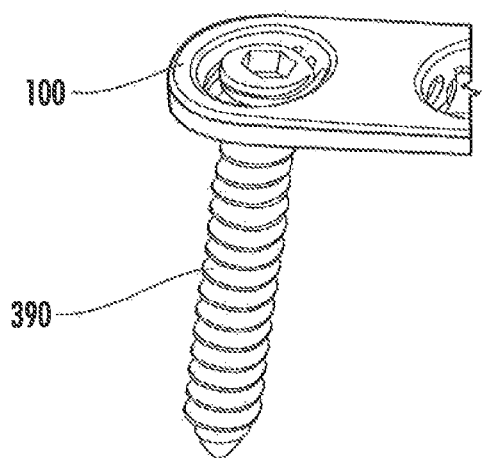
FIG. 17 is a perspective view of FIG. 16.
Figure 18:
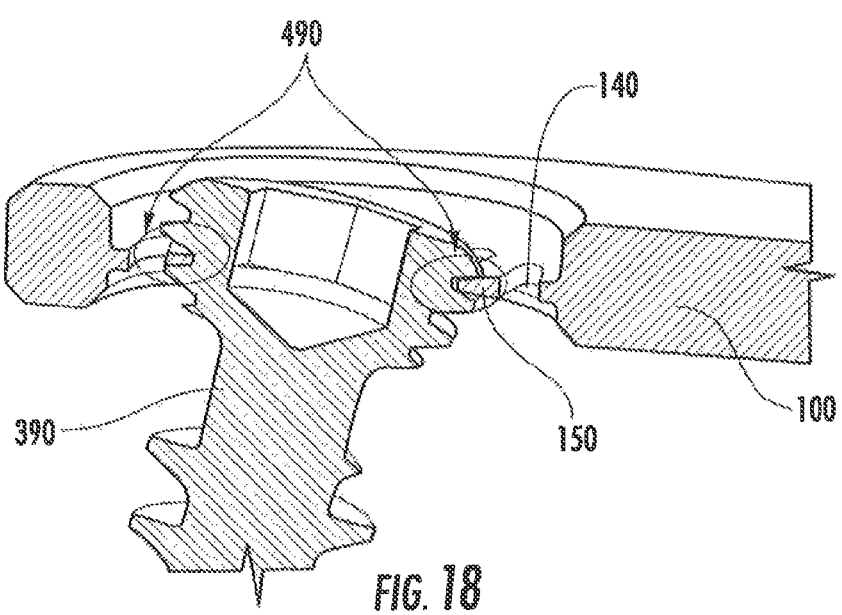
FIG. 18 is a detailed partial cross section view of FIG. 17.

FIGS. 16 through 18 show an assembly of a bone fixation device 390 and the bone plate 100. The bone fixation device 390 is a threaded head bone screw. FIGS. 16-18 show the bone fixation device in an angled position. For this image the angle is approximately 20 degrees. This 20 degree angle is not a limiting feature and is only used for demonstration purposes. A wide range of angles may exist between the bone fixation devices and bone plates of the present invention. FIG. 18 shows the engagement 490 between the beam member 150 and the head diameter 470 (see FIG. 11). It should be noted that as the bone fixation device is introduced at different angles into the passage hole, the beams 150 will engage various positions of the head of the screw 400. As the head 400 engages the locking mechanism, the beam moves to accommodate the needed engagement. The beam may move into the space above and/or below the beam member. However, the present invention also allows the beam when engaged with the bone fixation device to move into the predefined space allowing for a radial movement.

Figure 19:
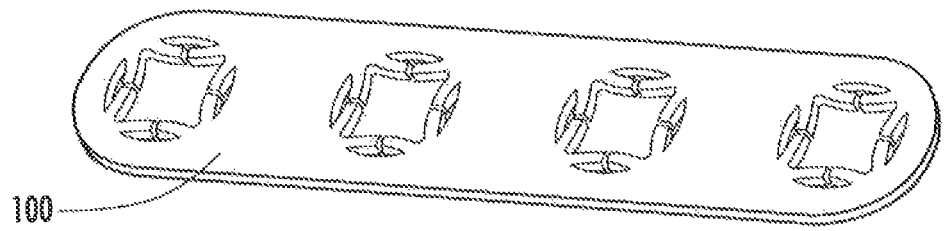
FIG. 19 is a perspective view of a third embodiment of a bone plate of the invention.
Figure 20:
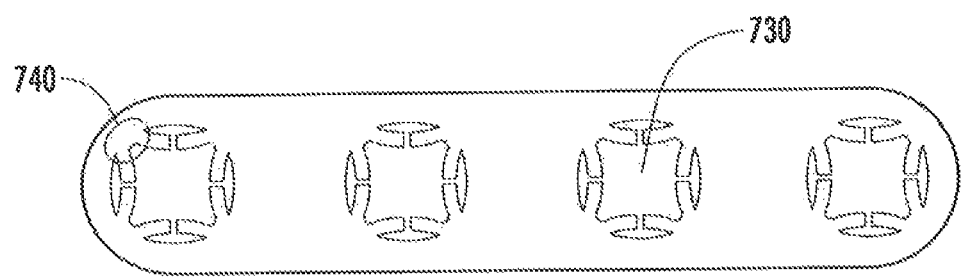
FIG. 20 is a top plan view of FIG. 19.
Figure 21:
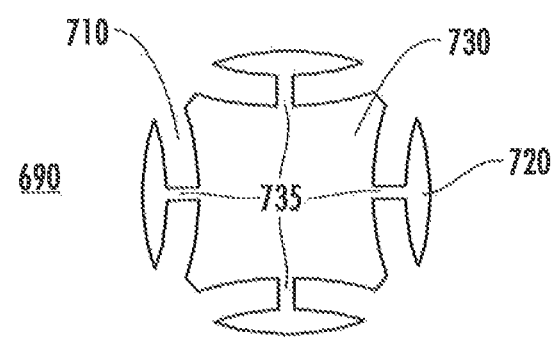
FIG. 21 is a detailed view illustrating the beam members according to the third embodiment of the invention shown in FIGS. 19 and 20.

A third embodiment of the locking mechanism is shown in FIGS. 19, 20 and 21. The locking mechanism 690 may be similar to that described in respect of other embodiments herein with the inclusion of an interruption 735. Interruption 735 divides the beam member 710 into two members, each member having only one connection point 740 as designated by the oval in FIG. 20. The interrupted beam member does not project toward the axis of the passage hole 730. The predefined space 720 has an interruption or connection space 735 to the passage hole 730. The beam members are allowed to move into the predefined space 720. Such an embodiment may be used for ease of manufacturing. Alternate embodiments may vary the size, geometry, configuration, volume, shape, perimeter, and/or other features of the predefined space and/or beam member. Furthermore, alternative embodiments may encompass any relationship between the number of beams, number of predefined spaces, size, geometry, configuration, volume, shape, perimeter, etc.

The present invention does not require a threaded feature in the implant. This allows for a number of different bone fixation devices to be used. It also allows for a substantially thinner implant than prior art locking mechanisms. The non-threaded aspect enables locking mechanisms to be manufactured using materials that were previously thought to be non-viable options due to the difficulty in producing typical locking mechanisms or the inability of the material to produce a durable lock. For example, materials like nitinol are very costly and difficult to thread and are typically not used where a locking interface is needed. Also, materials such as PEEK are not suitable for the locking mechanisms used by many prior art devices due to the destructive nature of the locking mechanism or the cantilevered geometry involved. Such geometries may fracture and break if produced in materials such as PEEK. Also, cross-threading, gouging, or stripping of PEEK may generate unwanted wear debris. Additionally, polymeric materials may not allow for a robust locking interface when used in conjunction with known locking mechanisms.

Figure 22:
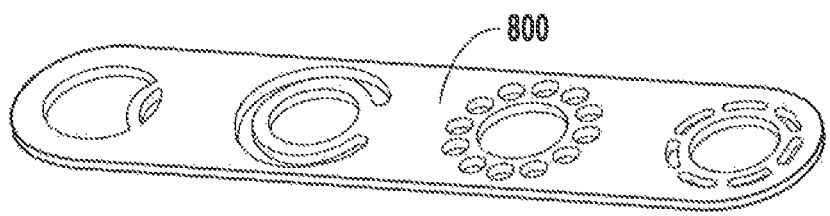
FIG. 22 is a perspective view of a bone plate with numerous examples of alternate embodiments of the multi-directional locking mechanism.
Figure 23:
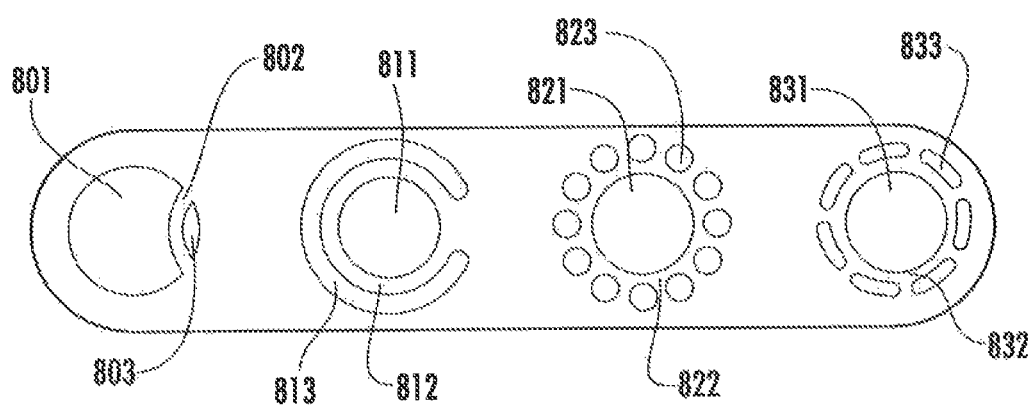
FIG. 23 is a top plan of the bone plate and locking mechanisms shown in FIG. 22.

FIGS. 22 and 23 show numerous alternate embodiments of the locking mechanism. All embodiments show varying size, geometry, configuration, volume, shape, perimeter, etc. of the passage holes 801, 811, 821, 831 predefined spaces 803, 813, 823, 833 and, beam members 802, 812, 822, 832. It should be noted that the beam member itself may also have a predefined space or a passage hole.

In FIGS. 31 and 32, an alternate embodiment is shown that may be manufactured as a laminate construct. Bone plate assembly 800 includes a top plate 830 and a bottom plate 840. When assembled, a top surface 810 is created from the top plate 830 and a bottom surface 820 is created from the bottom plate 840. A passage hole 850 is present as well as the beam member(s) 860 and the predefined space(s) 870. In this representation, the locking mechanism is part of the bottom plate 840 and the top plate 830 incorporates a through hole that aligns with the locking mechanism. Alternate embodiments could have part of the locking mechanism on one plate and other features on another plate. For example, one plate may have two beam members and two predefined spaces while another plate may have multiple beam members and predefined spaces such that when assembled, the various features of the locking mechanism are no longer co-linear. The laminate construct may be made up of multiple plates (i.e. more than one). The embodiment shown here consists of two plates. In other alternative embodiments, more than two plates may be secured together to form laminate constructs.

Figure 33:
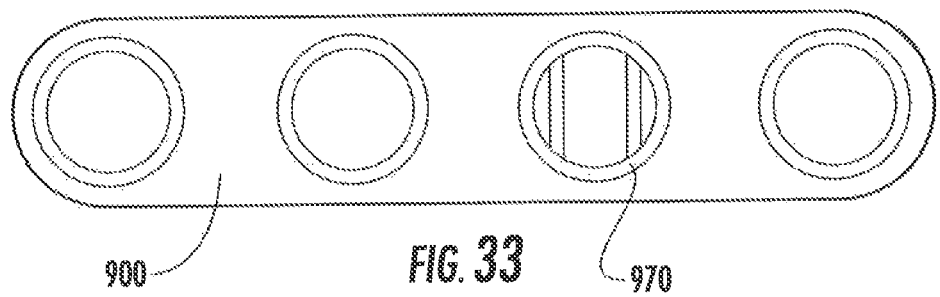
FIG. 33 is a top plan view of a bone plate showing an alternate embodiment of the present invention as an assembly.
Figure 34:
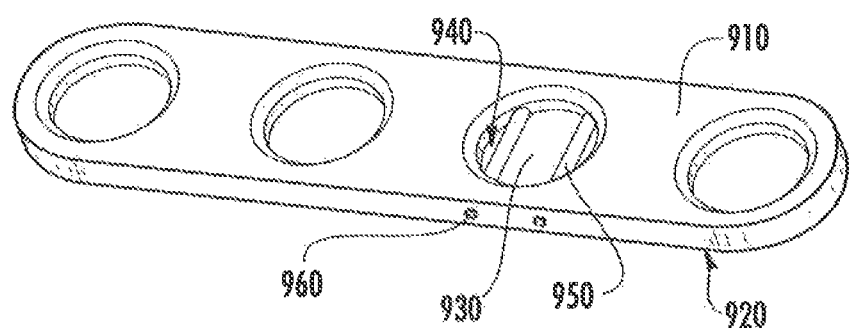
FIG. 34 is a perspective view of the embodiment shown in FIG. 33.
Figure 35:
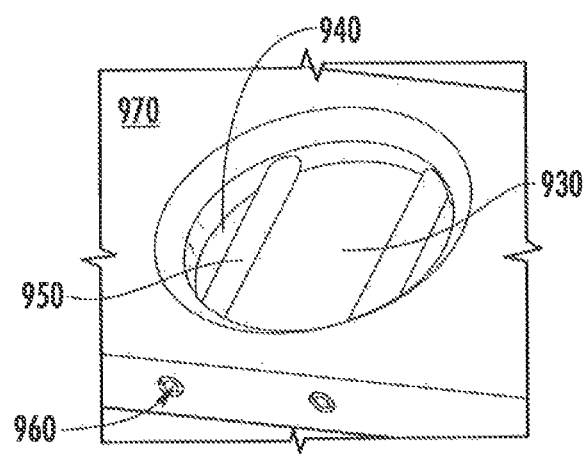
FIG. 35 is a partial detailed view of the embodiment shown in FIGS. 33 and 34.

The benefits and advantages of the locking mechanism of the invention can also be achieved as a permanent assembly. FIGS. 33, 34 and 35 show an embodiment of a bone plate 900 that has a locking mechanism 970 that comprises a passage hole 930. Passage hole 930 has a beam member 950 that is a component that is assembled to the plate. In this particular embodiment, the beam member 950 is a pin that is assembled into the bone plate 900 via a hole 960. This assembly creates a predefined space 940. This embodiment has the benefits and advantages described in connection with other embodiments herein. The beam members 950 may or may not be coplanar and/or coaxial. Beam members 950 may or may not be formed of the same material as the bone plate 900. Based on the disclosure herein, those skilled in the art will understand that an assembly construct can have a wide variety of sizes, geometries, configurations, volumes, shapes, perimeters, etc. This embodiment may or may not be combined with the embodiment described in FIGS. 31 and 32.

Figure 24:
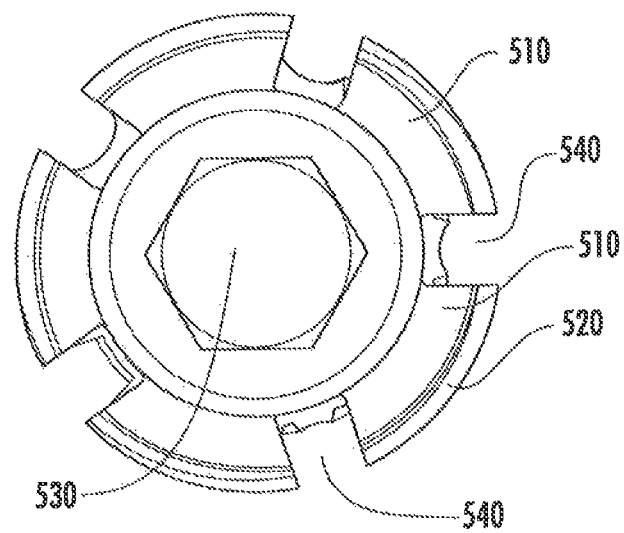
FIG. 24 is a top view of a bone fixation device with a predefined space and multiple beam members according to a fourth embodiment of the invention.
Figure 25:
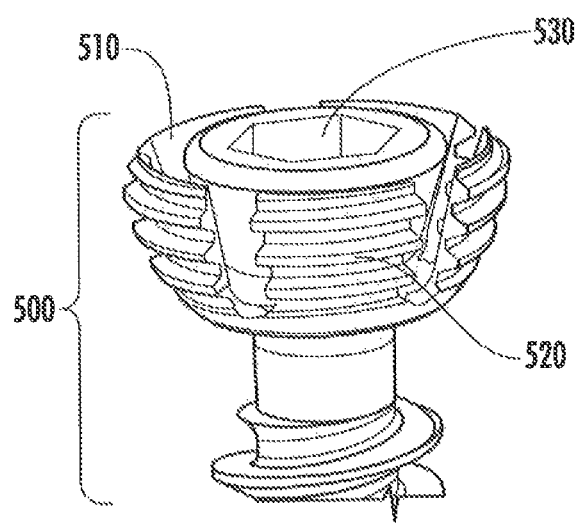
FIG. 25 is a perspective view of the embodiment shown in FIG. 24.
Figure 29:
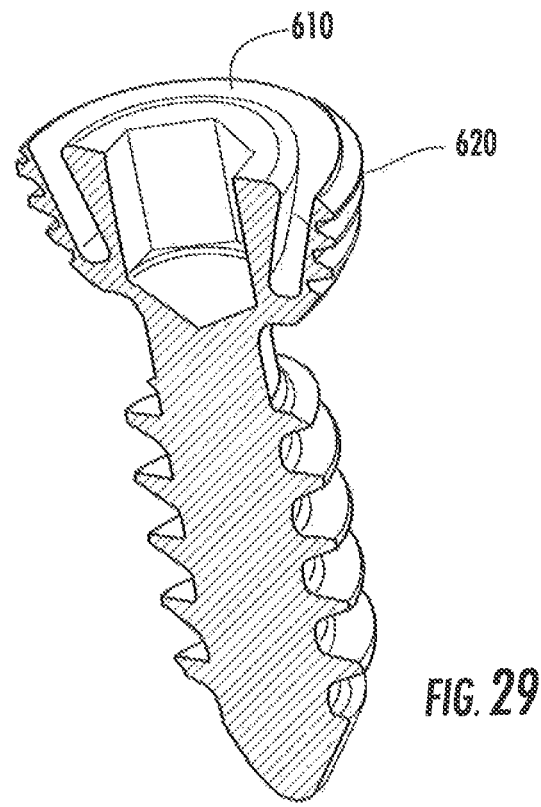
FIG. 29 is a perspective cross section view of the embodiment shown in FIG. 27.
Figure 30:
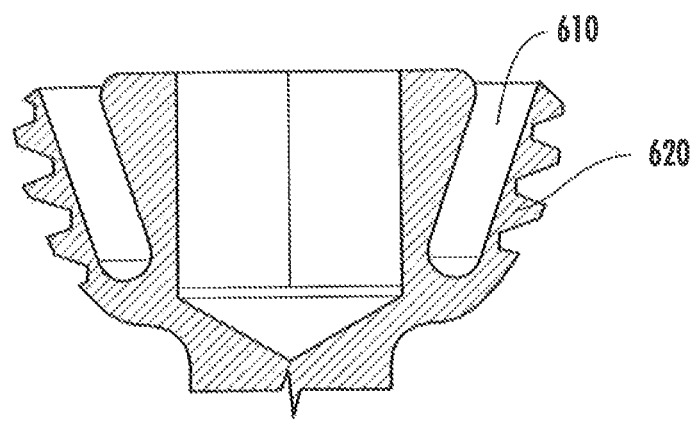
FIG. 30 is a detailed partial cross section view of the embodiment shown in FIG. 27.

The principles of the present invention can also be incorporated into the alternate bone fixation devices instead of or in addition to a bone plate. FIGS. 24-26 show an embodiment of a bone fixation device 500 that includes a predefined space 510 in the head of the bone fixation device. The predefined space 510 is open to the perimeter via the interruption 540. The beam member 520 is created and allowed to move into the predefined space when engaged into a bone plate. An alternate embodiment of a bone fixation device 600 incorporating the current invention is shown in FIGS. 27-30. The bone fixation device 600 includes a predefined space 610 in the head. In this embodiment, the predefined space 610 does not have an interruption, thereby creating a single beam member 620. The beam member 620 moves into the predefined space when engaged into the bone plate. The bone fixation devices described in FIGS. 24-30 show a mostly cylindrical head, but alternate embodiments could include bone fixation device heads that are non-circular in cross-sectional shape. For example, trilobular, elliptical, equilateral polygonal, or other cross sectional shapes may be used to form the head of the bone fixation device.

Figure 36B:
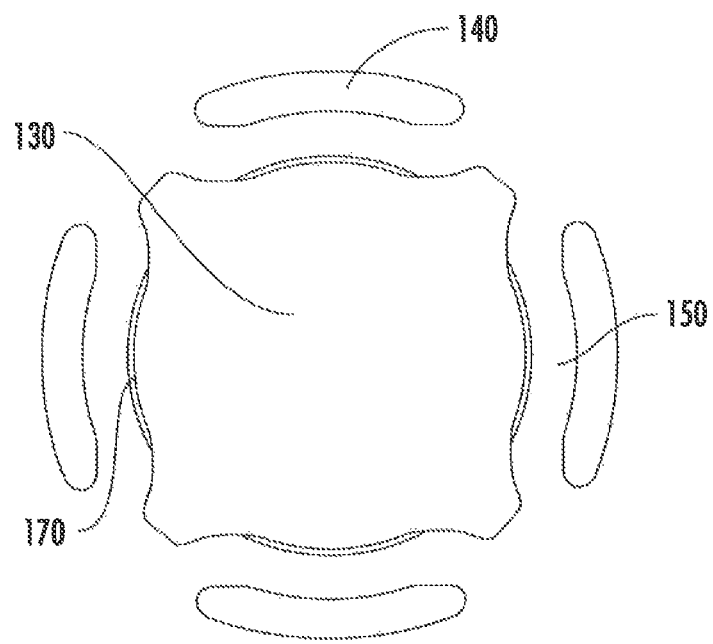
Figure 36C:
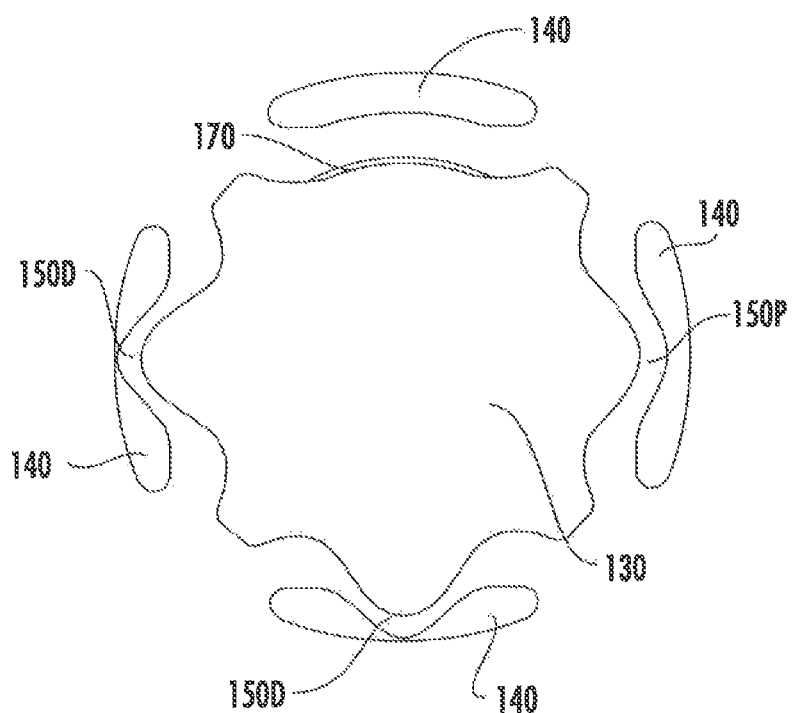
FIG. 36C illustrates the deformation of the beam members caused by insertion of a screw not necessarily perpendicular to a bone plate.

FIGS. 36A, 36B and 36C are provided to illustrate the deformation of the beam members 150 as a result of screwing in a bone fixation device 390. FIG. 36A is essentially a partial bottom view of FIG. 14 illustrating fixation device 390 in the locking mechanism elements. FIG. 36B illustrates the condition and positions of locking mechanism elements of FIG. 36A but without fixation device 390. As can be seen from both FIGS. 36A and 36B, fixation device 390 causes beam members 150 to be deflected into predefined spaces 140 and it causes optional lead-in features 170 to be deformed. This combination of deflection and deformation locks fixation device 390 into the locking mechanism, but either deflection or deformation can also be sufficient to cause locking. In FIG. 36C, beam members 150D have been deflected to a point where they have "bottomed out" in predefined spaces 140 and beam member 150P has also been substantially deflected but not bottomed out.

Figure 37A:
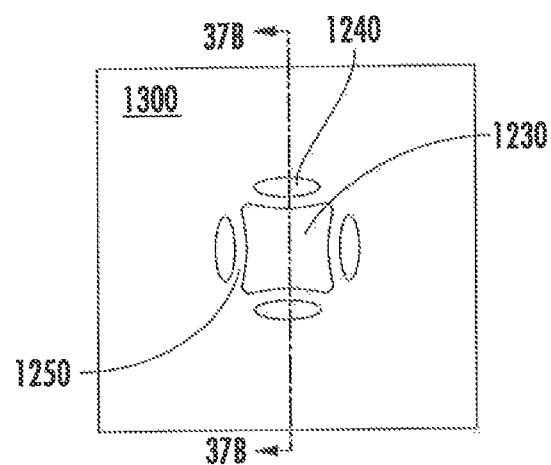
FIGS. 37A-37D illustrate a "blind hole" embodiment of the locking mechanism.
Figure 37B:
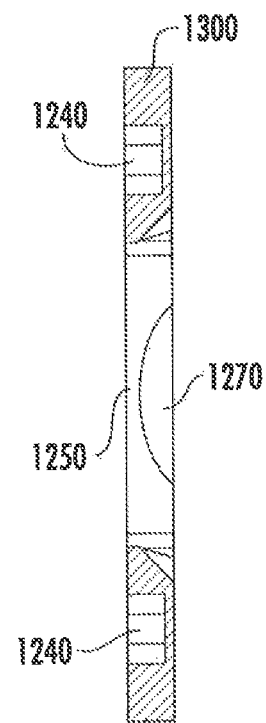
Figure 37C:
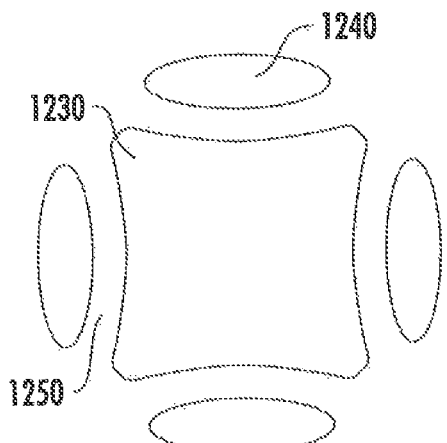
Figure 37D:
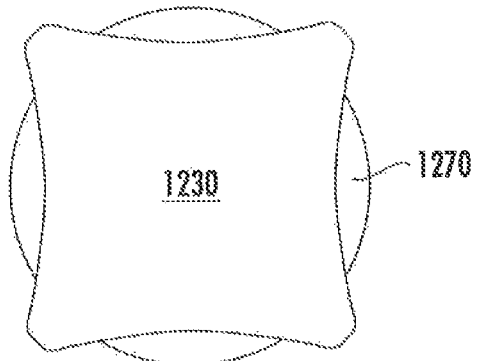

FIGS. 37A-37D illustrate a blind hole configuration wherein predefined spaces 1240 do not pass all the way through plate 1300. FIG. 37A is a top view of plate 1300 and FIG. 37C illustrates, independently of plate 1300, the elements of the locking mechanism, namely, opening 1230, predefined spaces 1240, beam members 1250 and countersink 1270. Section 37B shows predefined spaces 1240 that do not pass all the way through plate 1300. FIG. 37D is a bottom view of the elements of the locking mechanism of plate 1300.

FIG. 38A is a top plan view of mesh 1400 having locking mechanisms 300 of the type illustrated in FIG. 3. Connecting elements 1401 connect the locking mechanisms 300 to one another to make up the mesh. FIG. 38B is a perspective view of FIG. 38A.

Figure 39A:
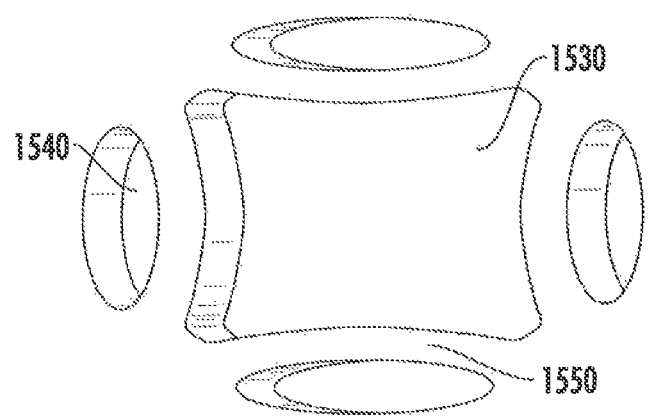
FIGS. 39A-39C illustrate a first embodiment of a locking mechanism having a non-orthogonal orientation.
Figure 39B:
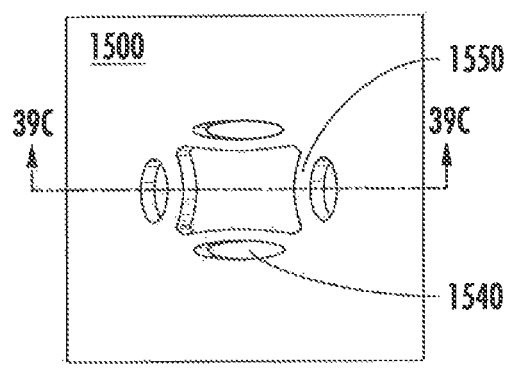
Figure 39C:
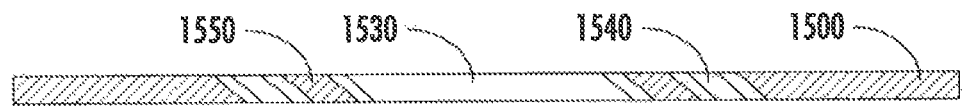

FIGS. 39A-39C illustrate a locking mechanism having a non-orthogonal orientation. FIG. 39B illustrates the locking mechanism in plate 1500. The elements of the locking mechanism independent of the plate are illustrated in FIG. 39A, namely, opening 1530, predefined spaces 1540 and beam members 1550. FIG. 39C is a section view of FIG. 39B.

Figure 40A:
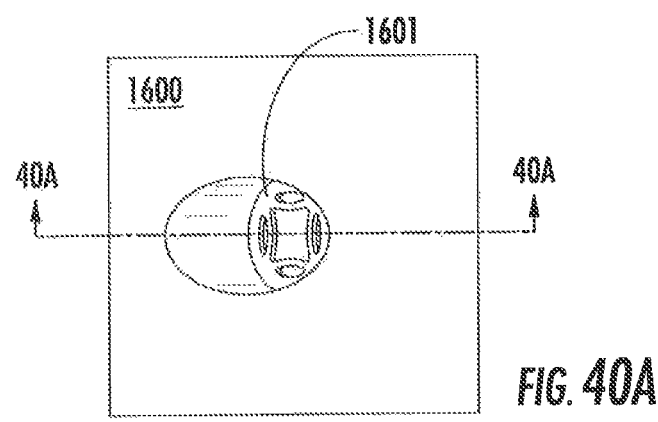
FIGS. 40A-40C illustrate a second embodiment of a locking mechanism having a non-orthogonal orientation.
Figure 40B:
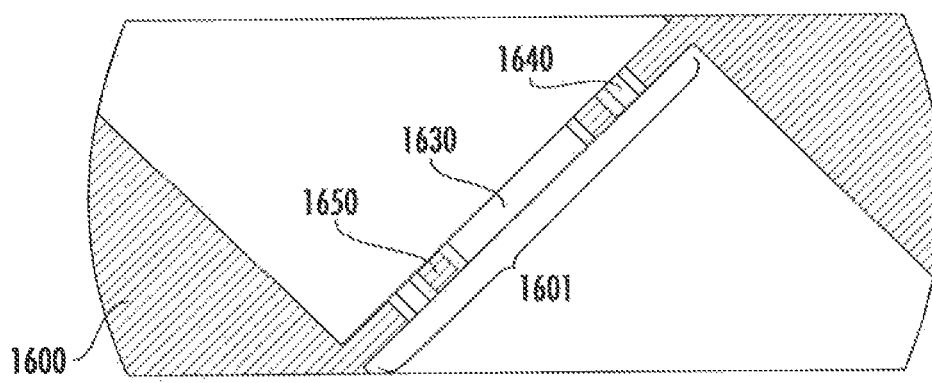
Figure 40C:
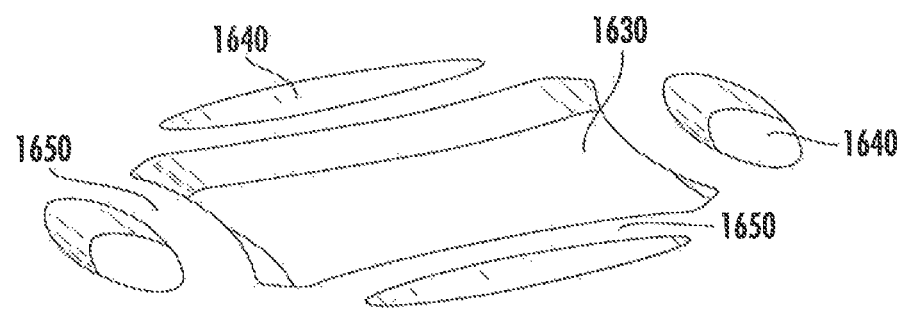

Another non-orthogonal locking mechanism is illustrated in FIGS. 40A-40C. Plate 1600 has a recessed locking mechanism 1601. The mechanism has an opening 1630, predefined spaces 1640 and beam members 1650. FIG. 40A is a top plan view of plate 1600 and FIG. 40B is a section view thereof. The elements of the locking mechanism are illustrated in FIG. 40C.

FIG. 41A is a top plan view of locking mechanism 1701 in curved plate 1700 and FIG. 41B is a section view thereof. The locking mechanism has an opening 1730, predefined spaces 1740 and beam members 1750.

Figure 42A:
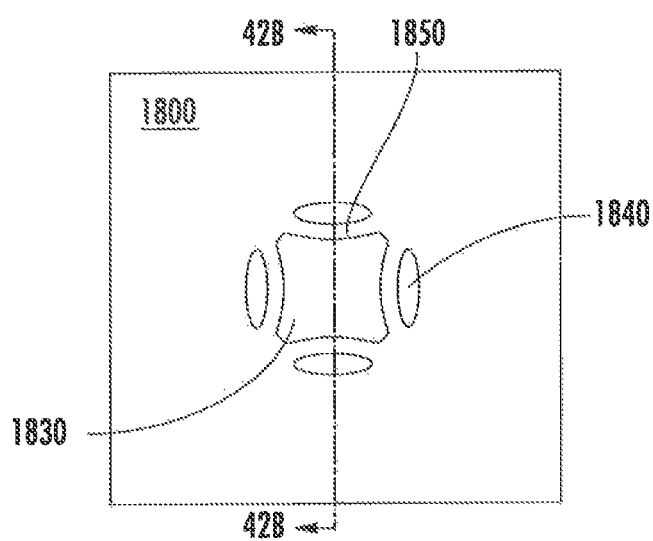
FIGS. 42A-42C illustrate an embodiment of the locking mechanism having "stacked" beam members.
Figure 42B:
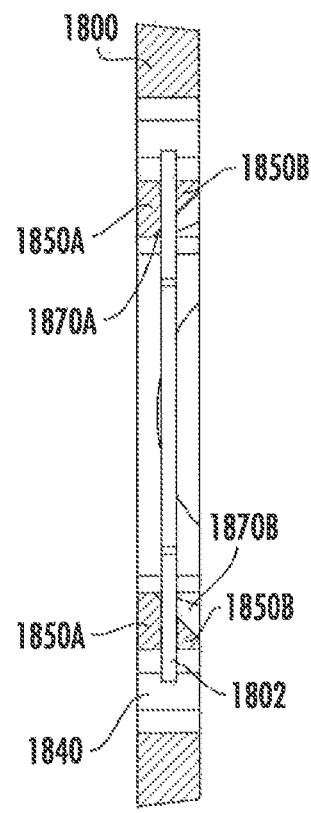
Figure 42C:
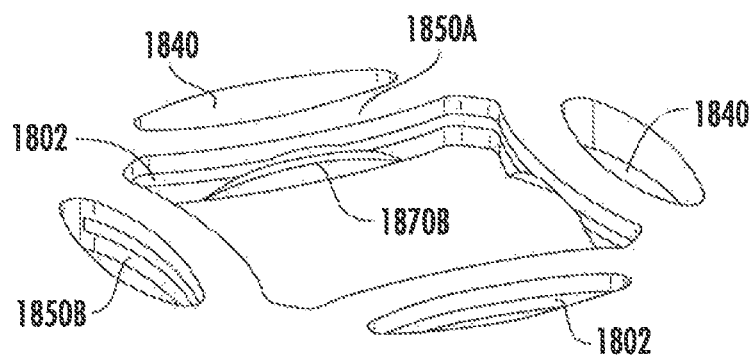

FIGS. 42A-42C illustrate a locking mechanism embodiment having stacked beam members 1850A and 1850B in a plate 1800. FIG. 42A is a top view of plate 1800 illustrating opening 1830, predefined spaces 1840 and beam members 1850A. In section view 42B and the perspective view of the locking mechanism elements 42C beam members 1850B are illustrated. Beam members 1850B have optional lead-in features 1870B and somewhat small optional lead-in features 1870A are in beam members 1850A. The stacked beam members are separated by space 1802. In this illustration there are two stacked beam members but there can be three or more as will be apparent to those having skill in the art based on the description and drawings herein.

Figure 43:
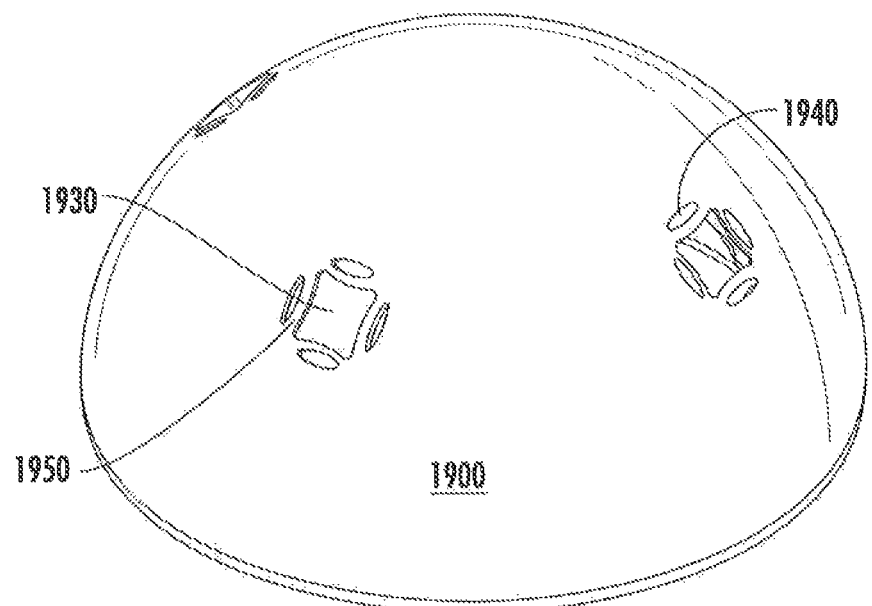
FIG. 43 is a top perspective view of an acetabular cup comprising polyaxial locking plates of the invention.
Figure 44:
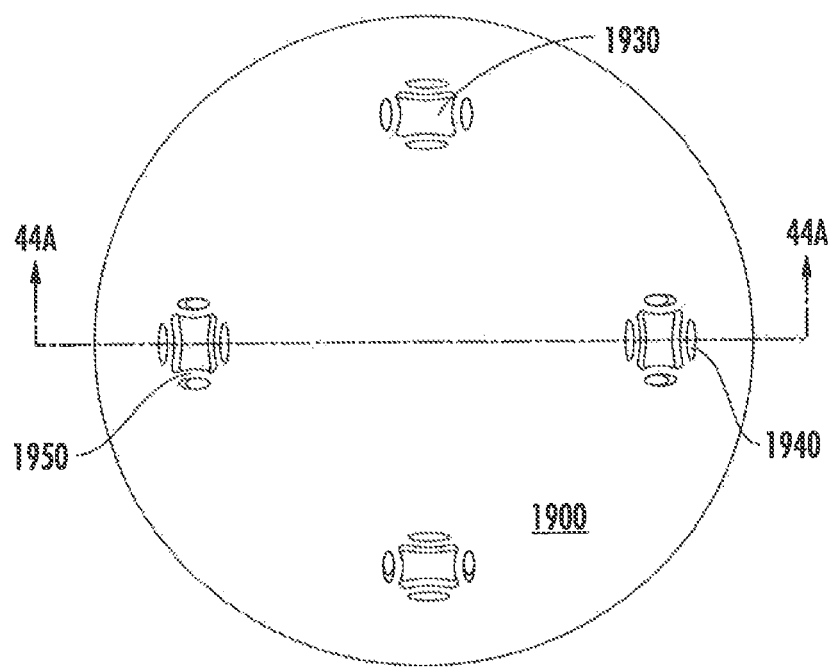
FIG. 44 is a top plan view of the acetabular cup of FIG. 43
Figure 44A:
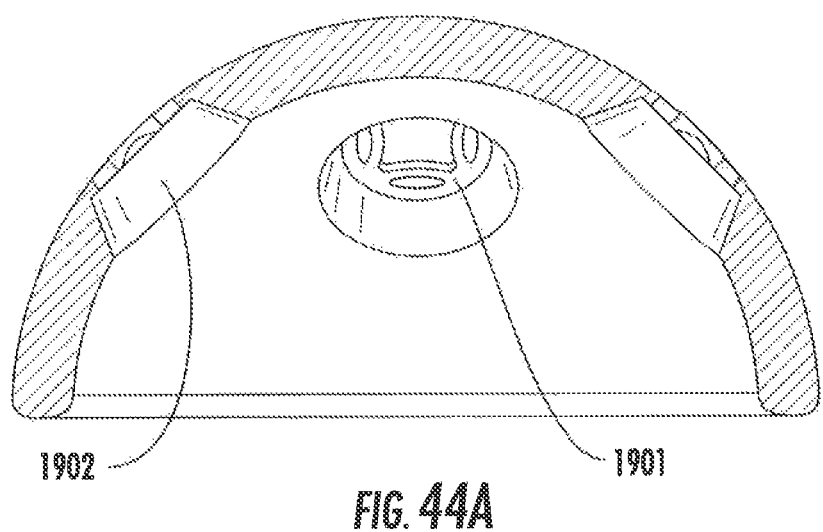
FIG. 44A is a section view of FIG. 44.
Figure 45:
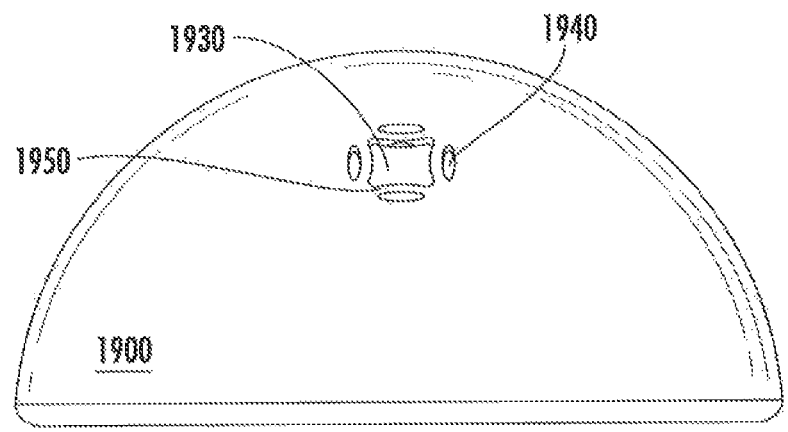
FIG. 45 is a side view of the acetabular cup of FIG. 43.
Figure 46:
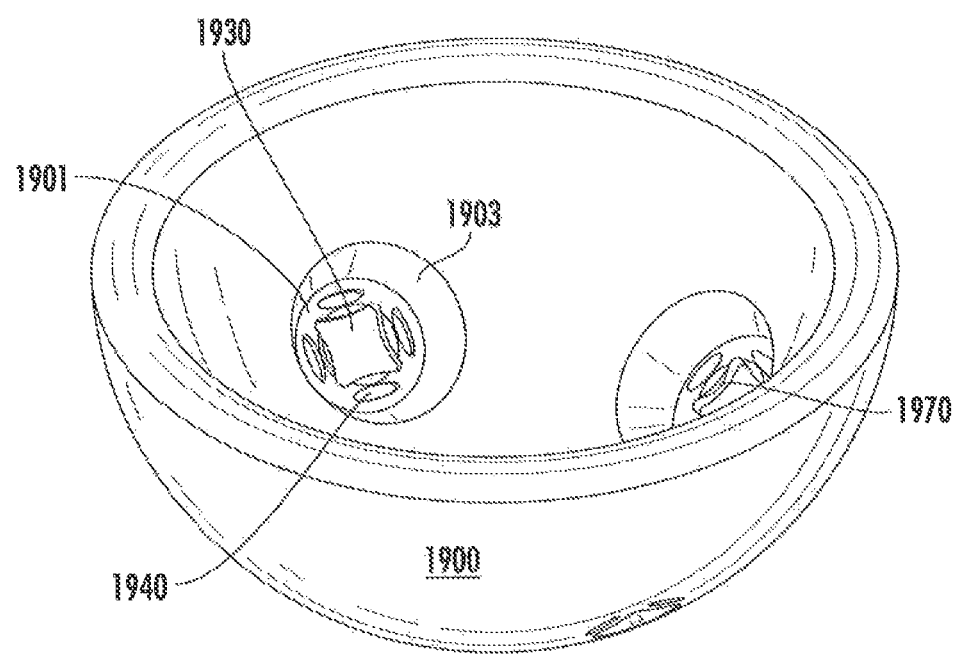
FIG. 46 is a bottom perspective view of the acetabular cup of FIG. 43.

FIG. 43 is a perspective top view of acetabular cup 1900 having locking mechanisms 1901 (see FIG. 44A). FIG. 44 is a top plan view of acetabular cup 1900 and FIG. 44A is a section view thereof. FIG. 45 is a side elevation view and FIG. 46 is a bottom perspective view of acetabular cup 1900. The locking mechanism 1901 is in a recess 1903 on the inside of acetabular cup 1900 and it is flush with the outside surface of the cup. The elements include opening 1930, predefined spaces 1940 and beam members 1950. Optional lead-in features 1970 are also shown.

Figure 47A:
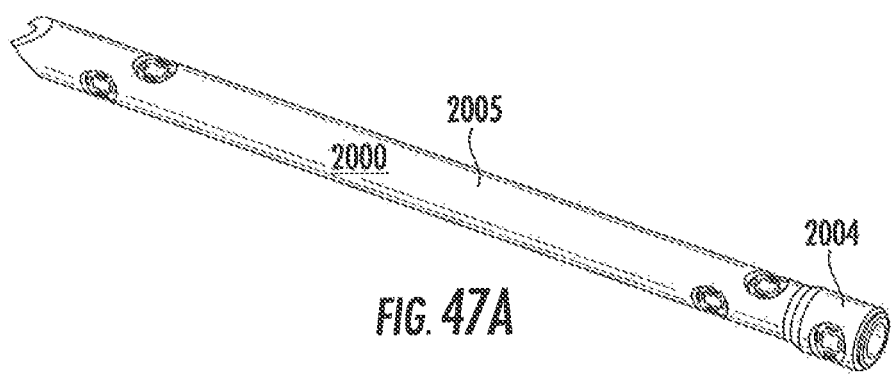
FIGS. 47A-47C illustrate an intramedullary nail comprising locking mechanisms of the invention.
Figure 47B:
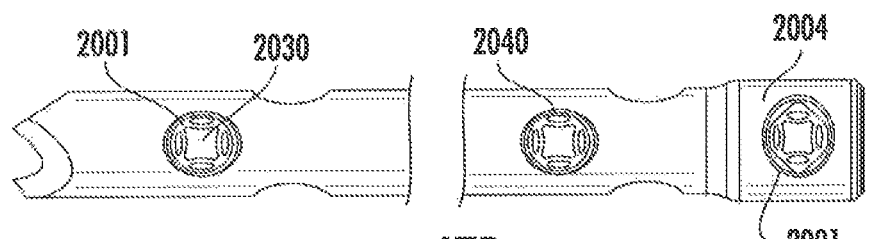
Figure 47C:
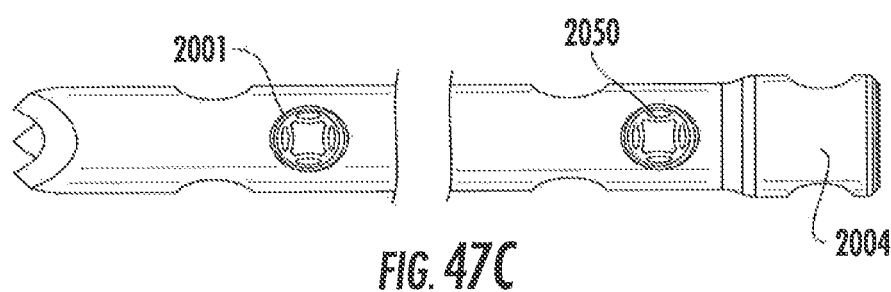

FIGS. 47A-47C illustrate intramedullary nail 2000. The nail is illustrated in perspective in FIG. 47A. FIG. 47B is a partial side elevation view and FIG. 47C is a partial top elevation view of nail 2000. The locking mechanisms 2001 are variously located along the nail as a matter of design choice depending upon the application for the nail. In this embodiment, there is a locking mechanism 2001 in nail head 2004 and other locking mechanisms 2001 are arranged along the shaft 2005. The locking mechanism 2001 is recessed below the nail surfaces and each mechanism contains an opening 2030, predefined spaces 2040 and beam members 2050.

As will be apparent to those having skill in the art based upon the description and drawings herein, the locking mechanisms of the present invention can be incorporated into any implant device that needs to be affixed to bone.

Various manufacturing methods may be used to make the components of the current invention. Some may result in beam members that are not flat in shape. The orientation of the individual beam members shown and described herein is not limiting. For example, if a bone plate was machined according to the principles of the current invention and then stamped to a final shape, the locking mechanism may also undergo a forming that would maintain parallelism between the top and bottom surfaces of a beam member, but the surfaces may not necessarily be flat.

What is claimed is:

1. A medical implant device comprising a locking mechanism for securing the medical implant device to a bone, the medical implant device comprising:
    an implant having a passage hole therethrough for receiving a bone fixation device at any of a plurality of angles relative to the implant, the passage hole having a central axis and a periphery;
    a locking mechanism comprising a first beam member, a second beam member, and a third beam member, each of which comprises a first side with a convex shape extending toward the central axis and facing toward the central axis to define a portion of the periphery, and a second side, opposite the first side, that defines a space adjacent to the second side; wherein each of the first beam member, the second beam member, and the third beam member is shaped and positioned such that, in response to advancement of the bone fixation device into the passage hole, the bone fixation device engages the first beam member, the second beam member, and the third beam member in a manner that deforms the first beam member, the second beam member, and the third beam member to cause, in each of the first beam member, the second beam member, and the third beam member, the second side to enter the space such that the first beam member, the second beam member, and the third beam member cooperate to resist withdrawal of the bone fixation device from the bone.

2. The medical implant device of claim 1, wherein the implant is selected from the group consisting of a bone plate, an intramedullary nail, a suture anchor, a prosthesis, and an element of a prosthesis and the bone fixation device is selected from the group consisting of bone screws, pins, and blades.

3. The medical implant device of claim 1, wherein the locking mechanism has a first thickness parallel to the central axis, and the implant has a second thickness, greater than the first thickness, parallel to the central axis, outside the locking mechanism.

4. The medical implant device of claim 3, wherein the locking mechanism is recessed relative to at least one of an upper surface of the implant and a lower surface of the implant.

5. The medical implant device of claim 1, wherein the first beam member comprises a lead-in feature on an edge of the first beam member adjacent to the passage hole;
wherein the lead-in feature is shaped and positioned to facilitate deformation of the first beam member in response to advancement of the bone fixation device into the passage hole.

6. The medical implant device of claim 1, wherein the first beam member comprises a first end secured relative to the periphery, and a second end, opposite to the first end, secured relative to the periphery.

7. The medical implant device of claim 1, wherein the first beam member comprises a first end secured relative to the periphery, and a second end, opposite to the first end, that moves away from the central axis in response to advancement of the bone fixation device into the passage hole.

8. The medical implant device of claim 1, wherein the first beam member is shaped to extend along a plane substantially perpendicular to the central axis.

9. The medical implant device of claim 1, further comprising the bone fixation device, the bone fixation device comprising a head having threading with a minor diameter sized to receive and engage the first beam member, the second beam member, and the third beam member in response to advancement of the bone fixation device into the passage hole.

10. The medical implant device of claim 9, wherein the minor diameter is tapered such that, during advancement of the bone fixation device into the passage hole, the minor diameter exerts increasing outward pressure on the first beam member, the second beam member, and the third beam member.

11. The medical implant device of claim 1, wherein:
each of the first beam member, the second beam member, and the third beam member is further shaped and positioned such that, in response to advancement of the bone fixation device into the passage hole, the bone fixation device engages the first beam member, the second beam member, and the third beam member in a manner that deforms each of the first beam member, the second beam member, and the third beam member in a first direction radially away from the central axis and in a second direction parallel to the central axis to cause the second side to enter the space; and
the first beam member, the second beam member, and the third beam member are further shaped and positioned to engage the bone fixation device such that the first beam member, the second beam member, and the third beam member remain deformed after advancement of the bone fixation device into the passage hole.

12. The medical implant device of claim 1, further comprising a bone fixation device comprising a threaded shaft and a threaded head, the threaded head comprising a plurality of threads;
wherein each of the first beam member, the second beam member, and the third beam member is further shaped and positioned such that, in response to advancement of the threaded head into the passage hole, the first side enters a gap between the threads such that the threaded head exerts radial force outward on the first beam member, the second beam member, and the third beam member to deform each of the first beam member, the second beam member, and the third beam member to cause the second side to enter the space such that the first beam member, the second beam member, and the third beam member frictionally engage the threaded head to resist withdrawal of the bone fixation device from the bone.

13. A bone fixation device having a head, the head having a head axis, a space radially disposed around the head axis, and a plurality of beam members radially disposed around the space;
wherein each of the beam members are sized and shaped to be deformed toward the head axis and into the space in response to advancement of the bone fixation device through a hole in an implant to affix the implant to a bone at any of a plurality of orientations of the bone fixation device relative to the implant, including orientations in which the head axis is nonparallel to a hole axis of the hole; and wherein each of the beam members comprises an outward-facing surface; and the outward-facing surfaces of the beam members cooperate to define a plurality of screw threads positioned such that, in response to advancement of the bone fixation device through the hole, the screw threads engage the hole to deform the beam members toward the head axis and into the space.

14. The bone fixation device of claim 13, wherein the beam member has an outer perimeter and comprises at least one interruption opening the space to the outer perimeter.

15. The bone fixation device of claim 13, wherein the beam member comprises:
a fixed end fixedly secured to a remainder of the bone fixation device; and
a free end displaced along the head axis, proximally or distally, from the fixed end.

16. A medical implant device comprising a locking mechanism for securing the medical implant device to a bone, the medical implant device comprising:
a bone fixation device comprising a threaded shaft and a threaded head, the threaded head comprising a plurality of threads;
an implant having a passage hole therethrough for receiving the bone fixation device at any of a plurality of angles relative to the implant, the passage hole having a central axis and a periphery;
a locking mechanism comprising a first beam member comprising a first side that protrudes toward the central axis and defines a portion of the periphery, and a second side, opposite the first side, that defines a space adjacent to the second side;
wherein the first beam member is shaped and positioned such that, in response to advancement of the threaded head into the passage hole, the first side enters a space between the threads such that the threaded head exerts radial force outward on the first beam member to deform the first beam member to cause the second side to enter the space such that the first beam member frictionally engages the threaded head to resist withdrawal of the bone fixation device from the bone.

17. The medical implant device of claim 16, wherein the first beam member comprises a first end secured relative to the periphery, and a second end, opposite to the first end, secured relative to the periphery.

18. The medical implant device of claim 16, wherein the first beam member comprises a first end secured relative to the periphery, and a second end, opposite to the first end, that moves away from the central axis in response to advancement of the bone fixation device into the passage hole.

19. The medical implant device of claim 16, wherein the first beam member is shaped to extend along a plane substantially perpendicular to the central axis.

\* \* \* \* \*